(12) United States Patent
Goetz et al.

(10) Patent No.: US 7,819,909 B2
(45) Date of Patent: Oct. 26, 2010

(54) THERAPY PROGRAMMING GUIDANCE BASED ON STORED PROGRAMMING HISTORY

(75) Inventors: Steven M. Goetz, Brooklyn Center, MN (US); Michael T. Lee, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 602 days.

(21) Appl. No.: 11/388,227

(22) Filed: Mar. 23, 2006

(65) Prior Publication Data

US 2006/0235472 A1    Oct. 19, 2006

Related U.S. Application Data

(63) Continuation-in-part of application No. 11/186,383, filed on Jul. 20, 2005.

(60) Provisional application No. 60/589,348, filed on Jul. 20, 2004.

(51) Int. Cl.
 *A61N 1/36* (2006.01)
(52) U.S. Cl. .................. 607/1; 607/2; 607/46; 607/59; 607/66; 607/148
(58) Field of Classification Search .................. 607/2
 See application file for complete search history.

(56) References Cited

U.S. PATENT DOCUMENTS

| | | | |
|---|---|---|---|
| 4,515,158 A | 5/1985 | Patrick et al. | |
| 4,520,825 A | 6/1985 | Thompson et al. | |
| 4,549,548 A | 10/1985 | Wittkampf et al. | |
| 4,958,632 A | 9/1990 | Duggan | |
| 5,033,469 A | 7/1991 | Brodard | |
| 5,159,926 A | 11/1992 | Ljungstroem | |
| 5,300,096 A | 4/1994 | Hall et al. | |
| 5,350,414 A | 9/1994 | Kolen | |
| 5,370,672 A | 12/1994 | Fowler et al. | |
| 5,402,070 A * | 3/1995 | Shelton et al. | ............... 324/433 |
| 5,443,486 A | 8/1995 | Hrdlicka et al. | |
| 5,513,645 A | 5/1996 | Jacobson et al. | |
| 5,653,739 A | 8/1997 | Maurer et al. | |

(Continued)

FOREIGN PATENT DOCUMENTS

EP    0 730 882    9/1996

(Continued)

OTHER PUBLICATIONS

Office Action dated Apr. 11, 2008 for U.S. Appl. No. 10/406,039, (19 pgs.).

(Continued)

*Primary Examiner*—Carl H Layno
*Assistant Examiner*—Deborah Malamud
(74) *Attorney, Agent, or Firm*—Shumaker & Sieffert, P.A.

(57) ABSTRACT

A programming device used to program delivery of therapy to a patient by a medical device, such as an implantable neurostimulator or pump, maintains or accesses a programming history for the patient. The programming history may take the form of a record of programs, e.g., combinations of therapy parameters, tested during one or more prior programming sessions. The programming device may analyze, or otherwise use the programming history to provide guidance information to a user, such as a clinician, which may assist the user in more quickly identifying one or more desirable programs during a current programming session.

32 Claims, 21 Drawing Sheets

U.S. PATENT DOCUMENTS

| | | | |
|---|---|---|---|
| 5,716,384 A | 2/1998 | Snell | |
| 5,722,999 A | 3/1998 | Snell | |
| 5,755,736 A | 5/1998 | Gillberg et al. | |
| 5,755,745 A | 5/1998 | McGraw et al. | |
| 5,775,331 A | 7/1998 | Raymond et al. | |
| 5,776,171 A | 7/1998 | Peckham et al. | |
| 5,776,173 A | 7/1998 | Madsen, Jr. et al. | |
| 5,807,397 A | 9/1998 | Barreras | |
| 5,836,987 A * | 11/1998 | Baumann et al. | 607/17 |
| 5,836,989 A | 11/1998 | Shelton | |
| 5,843,142 A | 12/1998 | Sultan | |
| 5,891,178 A | 4/1999 | Mann et al. | |
| 5,893,883 A | 4/1999 | Torgerson et al. | |
| 5,938,690 A | 8/1999 | Law et al. | |
| 6,027,456 A | 2/2000 | Feler et al. | |
| 6,035,233 A * | 3/2000 | Schroeppel et al. | 600/515 |
| 6,044,303 A | 3/2000 | Agarwala et al. | |
| 6,052,624 A | 4/2000 | Mann | |
| 6,058,328 A * | 5/2000 | Levine et al. | 607/14 |
| 6,120,467 A | 9/2000 | Schallhorn | |
| 6,175,764 B1 | 1/2001 | Loeb et al. | |
| 6,205,359 B1 | 3/2001 | Boveja | |
| 6,212,427 B1 * | 4/2001 | Hoover | 600/515 |
| 6,249,703 B1 | 6/2001 | Stanton et al. | |
| 6,308,100 B1 | 10/2001 | Er et al. | |
| 6,308,102 B1 | 10/2001 | Sieracki et al. | |
| 6,321,117 B1 | 11/2001 | Koshiol et al. | |
| 6,327,501 B1 | 12/2001 | Levine et al. | |
| 6,341,236 B1 | 1/2002 | Osorio et al. | |
| 6,381,496 B1 | 4/2002 | Meadows et al. | |
| 6,393,325 B1 | 5/2002 | Mann et al. | |
| 6,440,090 B1 | 8/2002 | Schallhorn | |
| 6,473,653 B1 | 10/2002 | Schallhorn et al. | |
| 6,480,743 B1 | 11/2002 | Kirkpatrick et al. | |
| 6,516,227 B1 | 2/2003 | Meadows et al. | |
| 6,558,321 B1 * | 5/2003 | Burd et al. | 600/300 |
| 6,564,807 B1 | 5/2003 | Schulman et al. | |
| 6,587,724 B2 | 7/2003 | Mann | |
| 6,609,031 B1 | 8/2003 | Law et al. | |
| 6,609,032 B1 | 8/2003 | Woods et al. | |
| 6,620,151 B2 | 9/2003 | Blischak et al. | |
| 6,654,642 B2 | 11/2003 | North et al. | |
| 7,317,948 B1 * | 1/2008 | King et al. | 607/62 |
| 2002/0049481 A1 | 4/2002 | Conley et al. | |
| 2002/0107553 A1 | 8/2002 | Hill et al. | |
| 2002/0115939 A1 | 8/2002 | Mulligan et al. | |
| 2002/0116036 A1 | 8/2002 | Daignault, Jr. et al. | |
| 2002/0165586 A1 | 11/2002 | Hill et al. | |
| 2002/0169484 A1 | 11/2002 | Mathis et al. | |
| 2003/0004549 A1 | 1/2003 | Hill et al. | |
| 2003/0028223 A1 | 2/2003 | Olson | |
| 2003/0036783 A1 | 2/2003 | Bauhahn et al. | |
| 2003/0065370 A1 | 4/2003 | Lebel et al. | |
| 2003/0139785 A1 | 7/2003 | Riff et al. | |
| 2003/0171791 A1 | 9/2003 | KenKnight et al. | |
| 2004/0111131 A1 | 6/2004 | Hu et al. | |
| 2004/0143302 A1 | 7/2004 | Sieracki et al. | |
| 2004/0158298 A1 | 8/2004 | Gliner et al. | |
| 2004/0199215 A1 | 10/2004 | Lee et al. | |
| 2004/0199216 A1 | 10/2004 | Lee et al. | |
| 2004/0199217 A1 | 10/2004 | Lee et al. | |
| 2004/0199218 A1 | 10/2004 | Lee et al. | |
| 2005/0177206 A1 | 8/2005 | North et al. | |
| 2005/0209655 A1 | 9/2005 | Bradley et al. | |
| 2005/0283210 A1 | 12/2005 | Blischak et al. | |
| 2006/0020292 A1 | 1/2006 | Goetz et al. | |

FOREIGN PATENT DOCUMENTS

| | | |
|---|---|---|
| EP | 1 249 254 | 10/2002 |
| EP | 1 304 137 | 4/2003 |
| WO | WO 97/43002 | 11/1997 |
| WO | WO 98/29160 | 7/1998 |
| WO | WO 01/93953 | 12/2001 |
| WO | WO 02/09808 | 2/2002 |
| WO | WO 2004/041352 | 5/2004 |
| WO | WO 2004/047629 | 6/2004 |
| WO | WO 2004/093983 | 11/2004 |

OTHER PUBLICATIONS

Responsive Amendment dated Jul. 8, 2008 for U.S. Appl. No. 10/406,039 (23pgs.).

Notification of Transmittal of the International Search Report and the Written Opinion of the International Search Authority or the Declaration for PCT/US2007/002240, dated Jul. 13, 2007 (10 pgs.).

Notification of Transmittal of the International Preliminary Report on Patentability dated Mar. 7, 2008 for Application No. PCT/US2007/002240 (9 pgs.).

Robin et al., "A New Implantable Microstimulator Dedicated to Selective Stimulation of the Bladder," Proceedings—19$^{th}$ International Conference—IEEE/EMBS Oct. 30-Nov. 2, 1997, Chigaco, IL, pp. 1792-1795.

"GenesisXP™ Neurostimulation Systems," Implantable Therapies for Chronic Pain and Neurological Disorders, http://www.ans medical.com/physicians/GenesisXPSystem/XPOverview.cfm Dec. 3, 2002.

"PainDoc® Computerized Support System," Implantable Therapies for Chronic Pain and Neurological Disorders, http://www.ans-medical.com/physicians/PainDoc/PainDoc.html Dec. 3, 2002.

"MultiStim®," Implantable Therapies for Chronic Pain and Neurological Disorders, http://www.ans medical.com/physicians/RenewRFSystem/MultiStim.html Dec. 3, 2002.

"PC-Stim®," Implantable Therapies for Chronic Pain and Neurological Disorders, http://www.ans medical.com/physicians/RenewRFSystem/PCStim.html Dec. 3, 2002.

"Renew® Neurostimulation System Overview," Implantable Therapies for Chronic Pain and Neurological Disorders, http://www.ans-rnedical.com/physicians/RenewRFSystem/SystemOverview.html Dec. 3, 2002.

Notification of Transmittal of the International Search Report and the Written Opinion of the International Search Authority or the Declaration for PCT/US2005/025892, dated Dec. 2, 2005 (13 pgs.).

Notification of Transmittal of the International Preliminary Report on Patentability from corresponding PCT Application Serial No. PCT/US2005/025892 mailed on Oct. 23, 2006 (9 pages).

Office Action dated Apr. 29, 2008 for U.S. Appl. No. 11/186,383 (11 pgs.).

Responsive Amendment dated Aug. 29, 2008 for U.S. Appl. No. 11/186,383 (19 pgs.).

Office Action for U.S. Appl. No. 10/406,039, mailed Oct. 22, 2008, 22 pages.

Amendment to Office Action for U.S. Appl. No. 10/406,039, filed Mar. 20, 2009, 22 pages.

Office Action for U.S. Appl. No. 11/186,383, mailed Jan. 7, 2009, 17 pages.

Amendment to Office Action for U.S. Appl. No. 11/186,383, filed Apr. 7, 2009, 25 pages.

Office Action for U.S. Appl. No. 101406,039, mailed Jun. 11, 2009, 15 pages.

Office Action for U.S. Appl. No. 11/186,383, mailed May 7, 2009, 13 pages.

Response to Office Action for U.S. Appl. No. 10/406,039, filed Sep. 11, 2009, 7 pages.

Amendment to Office Action for U.S. Appl. No. 11/186,383, filed Aug. 7, 2009, 29 pages.

Final Office Action for U.S. Appl. No. 10/406,039, mailed Jan. 22, 2010, 19 pages.

Response to final Office Action for U.S. Appl. No. 10/406,039, filed Mar. 22, 2010, 14 pages.

Responsive Amendment dated Oct. 24, 2008 for U.S. Appl. No. 11/388,227 (18 pgs.).

Final Office Action for U.S. Appl. No. 10/406,039, mailed Mar. 29, 2010, 20 pages.
Response to Final Office Action for U.S. Appl. No. 10/406,039, filed May 27, 2010, 14 pages.
Advisory Action for U.S. Appl. No. 10/406,039, mailed Jun. 7, 2010, 3 pages.
Final Office Action for U.S. Appl. No. 11/186,383, mailed Mar. 29, 2010, 15 pages.
Response to Final Office Action for U.S. Appl. No. 11/186,383, filed May 27, 2010, 20 pages.
Advisory Action for U.S. Appl. No. 11/186,383, mailed Jun. 14, 2010, 3 pages.
Request for Continued Examination (RCE), Response to Final Office Action and Advisory Action, for U.S. Appl. No. 11/186,383, filed Jul. 28, 2010, 27 pages.

* cited by examiner

| DATE | ELECTRODE CONFIGURATION | PULSE PARAMETERS | EFFECTIVENESS | SIDE EFFECTS | SENT HOME | USAGE | NOTES |
|---|---|---|---|---|---|---|---|
| 01/23/03 | - + o o o o o o<br>- + o o o o o o | AMP = 5.0<br>PW = 210<br>RATE = 30 | VAS = 6.4<br>OVERLAP = 60% | NONE | YES | 35% | |
| 01/23/03 | o o - + o o o o<br>o o - + o o o o | AMP = 4.5<br>PW = 210<br>RATE = 40 | VAS = 5.9<br>OVERLAP = 70% | MILD DISCOMFORT | NO | N/A | |
| ••• | ••• | ••• | ••• | ••• | ••• | ••• | |
| 11/15/03 | o o - + o o o o<br>o o - o o o o o | AMP = 4.5<br>PW = 230<br>RATE = 40 | VAS = 7.0<br>OVERLAP = 70% | NONE | YES | 50% | |

FIG. 11A

| DATE | ELECTRODE CONFIGURATION | PULSE PARAMETERS | EFFECTIVENESS | SIDE EFFECTS | SENT HOME | USAGE | NOTES |
|---|---|---|---|---|---|---|---|
| 01/23/03 | + - 0 0 0 0 | AMP = 5.0<br>PW = 210<br>RATE = 30 | RANGE = 3.5 – 5.8<br>RATING = 4.5 | LAUGHTER AT 4.5-5.8 | YES | 35% | |
| 01/23/03 | + 0 - 0 0 0 | AMP = 4.5<br>PW = 210<br>RATE = 40 | RANGE = 2.5 – 5.5<br>RATING = 4.6 | SPEECH AT 5.0-5.5 | NO | N/A | |
| ••• | ••• | ••• | ••• | ••• | ••• | ••• | |
| 11/15/03 | + 0 0 - 0 0 | AMP = 4.5<br>PW = 230<br>RATE = 40 | RANGE = 3.0 – 6.0<br>RATING = 3.9 | NONE | YES | 50% | |

FIG. 11B

THERAPY PROGRAMMING GUIDANCE BASED ON STORED PROGRAMMING HISTORY

This application is a continuation-in-part of U.S. application Ser. No. 11/186,383, filed Jul. 20, 2005, which claims the benefit of U.S. provisional application No. 60/589,348, filed Jul. 20, 2004. The entire content of both applications is incorporated herein by reference.

TECHNICAL FIELD

The invention relates to the delivery of therapy by medical devices and, more particularly, to programming the delivery of therapy by medical devices.

BACKGROUND

Medical devices that deliver a therapy to a patient often do so according to a program that includes a plurality of parameters. Each of the parameters of such a program defines an aspect of the therapy as delivered by the medical device according to that program. For example, the programs used by medical devices that deliver therapy in the form of electrical stimulation, such as neurostimulators, typically include parameters that define characteristics of the electrical stimulation waveform to be delivered. Where electrical stimulation is delivered in the form of electrical pulses, for example, the parameters for such a program may include a voltage or current amplitude, a pulse width, and a rate at which the pulses are to be delivered by the medical device. Further, where a medical device that delivers electrical stimulation is implantable and, as is typical for implantable neurostimulators, coupled to an electrode set including a plurality of electrodes, such a program may include an indication of the particular electrodes within the electrode set to be used to deliver the pulses, and the polarities of the selected electrodes. As another example, the programs used by medical devices that deliver therapy via infusion of a drug or other agent may include parameters that define flow rates, agent types or concentrations, and infusion type, e.g., continuous or bolus.

In most cases, a clinician creates the one or more programs that a medical device will use to deliver therapy to a patient during an initial programming session. In the case of implantable medical devices, the initial programming session typically occurs shortly after the device is implanted in the patient. The values for each of the parameters of a program may have a significant impact on the efficacy and side effects of the delivery of therapy according to that program. The process of selecting values for the parameters that provide adequate results can be time consuming. In particular, the process may require a great deal of trial and error testing of numerous potential combinations of parameter values before a "best" program is discovered. A "best" program may be a program that is better in terms of clinic efficacy versus side effects experienced than other programs tested. The process is particularly burdensome in the case of programming implantable neurostimulators for delivery of spinal cord stimulation (SCS) therapy, which are often coupled to an electrode set including eight or sixteen electrodes. The number of possible combinations of electrodes that could be tested during a programming session from set of that size is substantial, e.g., potentially on the order of tens or hundreds of thousands, or even millions of possible electrode combinations.

In some cases, the clinician may test combinations of parameter values, i.e., potential programs, by manually specifying each combination to test based on intuition or some idiosyncratic methodology, and recording notes on the efficacy and side effects of each combination after delivery of stimulation according to that combination. During a programming session, the clinician may be required to make notations describing the parameters of a number of tested programs and feedback received from the patient regarding the perceived efficacy side effects of each program. The clinician may then select the "best" program based on the notations.

Even after this often-lengthy process, the programs selected during an initial programming session may ultimately prove to be inadequate. The eventual inadequacy of the initial programming may be due to a variety of problems, including progression of symptoms and/or an underlying ailment, increased or changed symptoms or side effects during activities and/or postures that were not replicated in the clinic during the initial programming session, slow onset of side effects and, in the case of delivery of stimulation via electrodes located on implantable leads, lead migration. If the programs selected during an initial programming session prove to be inadequate, the patient must return to the clinic for a follow-up programming session. Multiple follow-up programming sessions may be required over the period of time that the medical device is used to deliver therapy to the patient.

During a follow-up programming session, the clinician may refer to any printed records, or his or her own memory of the re previous programming sessions, i.e., of the previously tested programs and their efficacy and side effects. However, printed records and clinician memory of previous programming sessions are often absent or inadequate, and provide little assistance in more quickly identifying desirable programs during a current programming session. Consequently, the clinician typically must start the time-consuming program selection process anew during each follow-up programming session.

SUMMARY

In general, the invention is directed to maintenance of a programming history for a patient. The programming history may be maintained or accessed by a programming device used to program delivery of therapy to a patient by a medical device, and may take the form of a record of programs, e.g., combinations of therapy parameters, tested during one or more prior programming sessions. The programming device may analyze, or otherwise use the programming history to provide guidance information to a user, such as a clinician, which may assist the user in more quickly identifying one or more desirable programs during the current programming session.

During a programming session, the clinician may specify a program using the programming device by selecting values for various program parameters. When a program is specified, the clinician may test the program by directing the programming device to control the medical device to deliver therapy according to the program to the patient. The clinician or patient may enter rating information into the programming device for each tested program. The rating information for a tested program may include information relating to effectiveness of delivery of neurostimulation therapy according to the program in treating symptoms of the patient, side effects experienced by the patient due to the delivery of neurostimulation therapy according to the program, the power consumption required for delivery of stimulation according to the program, or the like. During the programming session, the programming device may maintain a session log for that session with the patient that includes a listing of programs tested on the patient and rating information provided by the clinician or the patient for programs of the list. The listing may be ordered according to the rating information in order to facilitate the selection of programs from the list by the clinician.

The programming device may create the programming history during the initial programming session after the medical device is provided to, e.g., implanted in, the patient. The programming device may store all or selected ones of the programs within the session log for that session within programming history. Similarly, the programming device may include all or selected ones of the programs from the session logs for follow-up programming sessions within the programming history, or may update the programming history based on retesting of programs during a follow-up programming session. The programming history may include the information stored for a program in the session log, e.g., information describing the parameters and rating information for the program, and may include clinician comments regarding the program and concomitant therapies delivered with the program.

During a current programming session, the programming device may retrieve information relating to the extent or times of use for one or more programs that were sent home with the patient, e.g., that the medical device was programmed with, during a previous programming session, and may update the record for those programs within the programming history to include this usage information. The programming device may also retrieve patient diary information associated with the one or more programs, which may include subjective comments regarding efficacy, side-effects, use, or the like, recorded by a patient during use of the programs, e.g., outside of the clinic setting. The programming device may also include objective sensor information collected via physiological sensors during use of the programs outside of the clinic. Usage information, patient diary information and sensor information may be stored by, and therefore retrieved from, one or both of the medical device and another programming device used by the patient to control delivery of therapy by the medical device, e.g., a patient programming device.

The programming device may display the programming history to the clinician during the current programming session, and the display of the programming history may assist the clinician in more quickly identifying desirable programs during the current programming session. The programming device may receive selection of a particular field within the programming history, e.g., effectiveness or side effects, and may order the programming history according to the selected field.

The programming device may analyze the programming history and, during the current programming session, may provide guidance information to the clinician to guide the selection and testing of programs. For example, the programming device may compare program parameters entered by the clinician while attempting to create a new program to the programs stored within the programming history. The programming device may identify the same or similar programs within the programming history, and may bring the record of such programs within the programming history to the user's attention, e.g., by displaying the record or a message and a link thereto. The clinician's decision of whether to proceed to test the program being entered may be informed by the results, e.g., rating, usage or patient diary information, when the same or similar programs were previously tested or used. Further, the programming device may identify same or similar programs within the programming history based on entry of only a portion of the parameters of a complete program, and may provide the parameters that would recreate one of the programs identified in the programming history based on the comparison to the clinician. In this manner, the programming device may act as a program generation "wizard," allowing the clinician to decide whether to test the automatically completed program, or to manually complete the program with different parameter values.

As another example, during a previous programming session, or during use by the patient outside of the clinic, a program, group of programs, or particular program parameter value may have proven to be so ineffective or to have such undesirable side effects as to be "blacklisted" in the programming history. Blacklisting of programs or parameter values may be done automatically by the programming device based on rating information, or manually by the clinician. The programming device may provide, for example, a visual indication such as highlighting or a text message within the displayed programming history to indicate that program is blacklisted, and may also present such an indication during an attempt to create a program with the same or similar parameters during a current programming session. In some embodiments, the programming device may "lock-out" the blacklisted program, e.g., prevent creation of programs with the same or similar parameters to a blacklisted program. Where a set of similar programs are blacklisted, the programming device or clinician may determine that a particular value or range of values for one or more individual parameters should be blacklisted, and the programming device may provide similar indications or messages when blacklisted parameter values are selected, or may lock-out selection of blacklisted parameter values. Further, in embodiments in which the programming device directs or suggests testing of parameter combinations according to a protocol, the programming device may modify the protocol to skip blacklisted parameter values or programs.

As another example, the programming device may identify parameter values or ranges of parameter values that have not yet been tested or have not been frequently tested on the patient, and indicate these values or ranges to the clinician. The clinician may then choose to test programs that include under tested parameter values or parameter value ranges. Further, the programming device may modify a protocol to include such parameter values or parameter value ranges The programming device may perform a statistical or pattern matching analysis to correlate a parameter value or range of parameter values with rating information or usage information, e.g., an effectiveness or overall score, a particular side effect, or the amount of out of clinic use, and may provide guidance information to a user based on the results of the analysis. For example, the programming device may indicate that particular parameter values or ranges have proven effective, or have proven to be correlated with a particular side effect or severity of side effects. In some embodiments, the programming device may combine the identification of underutilized parameter values and such correlations to suggest untested programs, e.g., combinations of parameters, that may provide desirable efficacy and side effects as indicated by the correlations. Further, in embodiment in which the programming device directs or suggests testing of parameter combinations according to a protocol, the programming device may modify the protocol based on the correlations between parameter values or ranges and effectiveness or side effects. The programming device may perform such analysis on the current patient's programming history, or the programming histories for a plurality of patients, e.g., a plurality of patients with similar symptoms, medical device configurations, or the like.

In some embodiments, when a previously tested program is selected for retesting, the programming device may collect rating information after the program is retested. The programming device may then compare the currently collected rating information to previously collected rating information for the program. If the programming device identifies a significant change in the rating information over time, the programming device may alert the clinician of the possibility of, for example, symptom or disease progression, or lead failure or movement. Additionally or alternatively, the programming device may present trend charts or a diagram of rating information for one or more programs over time, which the clinician may use to detect, for example, symptom or disease progression, or lead failure or movement.

In one embodiment, the invention is directed to a method in which a programming history stored in a memory is analyzed, and guidance information is provided to a user based on the analysis. The programming history includes information describing therapy programs tested on a patient during at least one prior programming session, and the information stored for each of the programs within the programming history includes information describing a plurality of parameters that define delivery of therapy according to that program and rating information for that program.

In another embodiment, the invention is directed to a system that includes a user interface, and a memory that stores a programming history, wherein the programming history includes information describing therapy programs tested on a patient during at least one prior programming session, and the information stored for each of the programs within the programming history includes information describing a plurality of parameters that define delivery of therapy according to that program and rating information for that program. The device further comprises a processor to analyze a programming history provide guidance information to a user based on the analysis to guide the selection of therapy programs during a current programming session.

In an added embodiment, the invention is directed to a computer-readable medium comprising instructions that cause a processor to analyze a programming history stored in a memory, and provide guidance information to a user based on the analysis. The programming history includes information describing therapy programs tested on a patient during at least one prior programming session, and the information stored for each of the programs within the programming history includes information describing a plurality of parameters that define delivery of therapy according to that program and rating information for that program.

In another embodiment, the invention is directed to a method comprising controlling an implantable medical device to deliver therapy to a patient according to each of a plurality of programs with a programming device during a programming session, recording rating information for each of the plurality of therapy programs during the programming session within the programming device, receiving selection of a subset of the programs, storing the selected subset of the programs within in the implantable medical device, wherein the subset of the programs are available to be selected by the patient to control delivery of therapy by the implantable medical device, and, for at least the subset of the programs, storing information identifying the programs and rating information associated with the programs in a programming history for the patient within the implantable medical device.

In another embodiment, the invention is directed to a system comprising an implantable medical device that delivers a therapy to a patient, and a programming device. The programming device controls the implantable medical device to deliver the therapy to the patient according to each of a plurality of programs during a programming session, records rating information for each of the plurality of therapy programs during the programming session, receives selection of a subset of the programs, provides the selected subset of the programs to the implantable medical device, and, for at least the subset of the programs, provides information identifying the programs and rating information associated with the programs to the implantable medical device. The implantable medical device stores the subset of the programs provided by the programming device, and stores the information identifying the programs and rating information associated with the programs received from the programming device as a programming history for the patient In another embodiment, the invention is directed to a computer-readable medium comprising instructions. The instructions cause a programmable processor to control an implantable medical device to deliver therapy to a patient according to each of a plurality of programs with a programming device during a programming session, record rating information for each of the plurality of therapy programs during the programming session within the programming device, receive selection of a subset of the programs, store the selected subset of the programs within in the implantable medical device, wherein the subset of the programs are available to be selected by the patient to control delivery of therapy by the implantable medical device, and for at least the subset of the programs, store information identifying the programs and rating information associated with the programs in a programming history for the patient within the implantable medical device.

The invention may provide a number of advantages. For example, by maintaining programming history, a programming device may be able to provide guidance information to a user, such as a clinician. The guidance information may allow the user to avoid repeated testing of unsuccessful programs or parameter values, and to more quickly identify programs that are desirable in terms of efficacy and side effects during follow-up programming sessions. The maintenance of a programming history may be particularly advantageous in the case of implantable stimulators, such as implantable neurostimulators that deliver SCS or deep brain stimulation therapy, where each programming session could involve testing a very large number of potential programs and/or redundant testing of a plurality of programs.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 11A is a conceptual diagram illustrating display of an example stored programming history by a graphical user interface of a clinician programmer.

FIG. 11B is a conceptual diagram illustrating display of another example stored program history by a graphical user interface of a clinician programmer.

DETAILED DESCRIPTION

Figure 1:
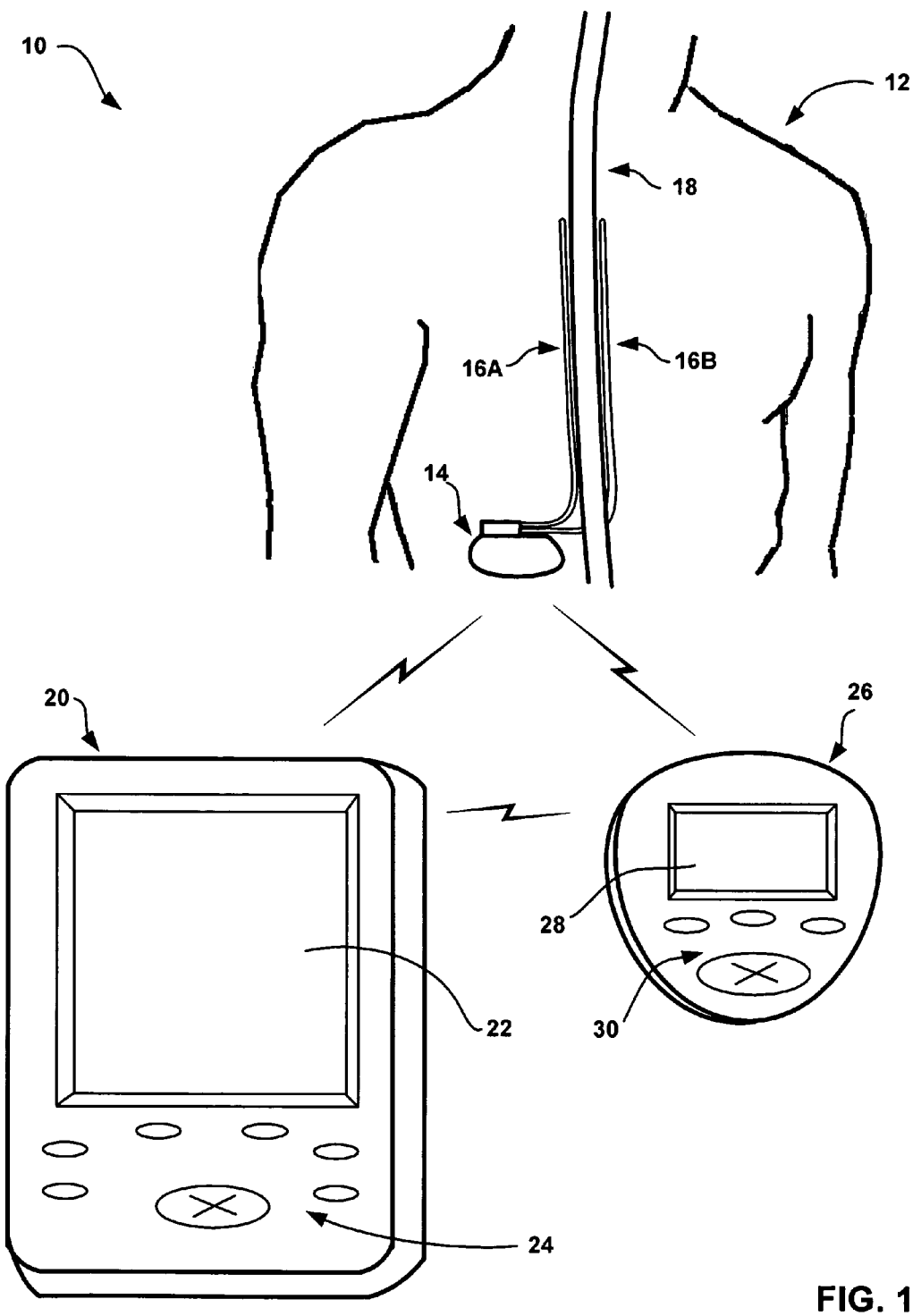
FIG. 1 is a conceptual diagram illustrating an example system for delivering therapy and programming delivery of a therapy to a patient.

FIG. 1 is a conceptual diagram illustrating an example system 10 for delivering therapy to and programming delivery of a therapy for a patient. System 10 includes an implantable medical device 14, which in the illustrated embodiment delivers neurostimulation therapy to patient 12. IMD 14 may be an implantable pulse generator, and may deliver neurostimulation therapy to patient 12 in the form of electrical pulses.

IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) or cortical stimulation therapy to patient 12 to, for example, treat movement disorders, such as tremor or Parkinson's disease, epilepsy, or mood disorders. As further examples, one or more leads 16 may be implanted proximate to the pelvic nerves (not shown) or stomach (not shown), and IMD 14 may deliver neurostimulation therapy to treat incontinence, sexual dysfunction, pelvic pain, gastroparesis, or obesity. Further, IMD 14 may be a cardiac pacemaker, and leads 16 may extend to a heart (not shown) of patient 12.

Moreover, the invention is not limited to systems that include an implantable pulse generator, or even an IMD. For example, in some embodiments, a system according to the invention may include an implanted or external pump that delivers a drug or other agent to a patient via a catheter, e.g., for alleviation of pain by intrathecal drug delivery. Systems for delivering therapy to and programming delivery of a therapy for a patient according to the invention may include any type of implantable or external medical device.

IMD 14 delivers neurostimulation therapy according to one or more programs. Each program may include values for a number of parameters, and the parameter values define the neurostimulation therapy delivered according to that program. In embodiments where IMD 14 delivers neurostimulation therapy in the form of electrical pulses, the parameters may include voltage or current pulse amplitudes, pulse widths, pulse rates, and the like. Further, each of leads 16 includes electrodes (not shown in FIG. 1), and the parameters for a program may include information identifying which electrodes have been selected for delivery of pulses according to the program, and the polarities of the selected electrodes. As another example, in embodiments which include a pump instead of or in addition to a neurostimulator, program parameters may define flow rates, agent types or concentrations, or infusion types, e.g., continuous or bolus.

System 10 also includes a clinician programmer 20. Clinician programmer 20 may, as shown in FIG. 1, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using a peripheral pointing devices, such as a stylus or mouse. Keypad 24 may take the form of an alphanumeric keypad or a reduced set of keys associated with particular functions. Display 22 may also present so-called soft keys for selection by the user.

A clinician (not shown) may use clinician programmer 20 to program neurostimulation therapy for patient 12. As will be described in greater detail below, the clinician may select existing programs or specify programs by selecting program parameter values, and test the selected or specified programs on patient 12. The clinician may receive feedback from patient 12, and store information identifying the programs and rating information associated with the programs as a session log for patient 12, either in a fixed or removable memory of the clinician programmer, or within a memory of another computing device coupled to the clinician programmer, e.g., via a network. The clinician may use the session log to more quickly select one or more effective programs to be used for delivery of neurostimulation therapy to patient 12 by IMD 14 outside of the clinic.

System 10 also includes a patient programmer 26, which also may, as shown in FIG. 1, be a handheld computing device. Patient programmer 26 may also include a display 28 and a keypad 30, to allow patient 12 to interact with patient programmer 26. In some embodiments, display 26 may be a touch screen display, and patient 12 may interact with patient programmer 26 via display 28. Patient 12 may also interact with patient programmer 26 using peripheral pointing devices, such as a stylus or mouse.

Patient 12 may use patient programmer 26 to control the delivery of neurostimulation therapy by IMD 14. Patient 12 may use patient programmer 26 to activate or deactivate neurostimulation therapy and, as will be described in greater detail below, may use patient programmer 26 to select the program that will be used by IMD 14 to deliver neurostimulation therapy at any given time. Further, patient 12 may use patient programmer 26 to make adjustments to programs, such as amplitude or pulse rate adjustments.

Programs selected during a programming session using clinician programmer 20 may be transmitted to and stored within one or both of patient programmer 26 and IMD 14. Where the programs are stored in patient programmer 26, patient programmer 26 may transmit the programs selected by patient 12 to IMD 14 for delivery of neurostimulation therapy to patient 12 according to the selected program. Where the programs are stored in IMD 14, patient programmer 26 may display a list of programs stored within IMD 14 to patient 12, and transmit an indication of the selected program to IMD 14 for delivery of neurostimulation therapy to patient 12 according to the selected program.

IMD 14, clinician programmer 20 and patient programmer 26 may, as shown in FIG. 1, communicate via wireless communication. Clinician programmer 20 and patient programmer 26 may, for example, communicate via wireless communication with IMD 14 using RF telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols. Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As will be described in greater detail below, clinician programmer 20 may maintain a programming history for patient 12, which may take the form of a record of programs, e.g., combinations of therapy parameters, tested during one or more prior programming sessions. Clinician programmer 20 may create the programming history during the initial programming session that occurs after IMD 14 is implanted in patient 12. Clinician programmer 20 may store all or selected ones of the programs within the session log for that session within programming history. Similarly, clinician programmer may include all or selected ones of the programs from the session logs for follow-up programming sessions within the programming history, or may update the programming history based on retesting of programs during a follow-up programming session. The programming history may include the information stored for a program in the session log, e.g., information describing the parameters and rating information for the program, and may include clinician comments regarding the program. Clinician programmer 20 may store the programming history within, for example, a fixed or removable memory of the clinician programmer, patient programmer 26, IMD 14, or a memory of another computing device coupled to the clinician programmer, e.g., via a network. When not stored within clinician programmer 20, the clinician programmer may retrieve the programming history for use during a current programming session.

During a current programming session, clinician programmer 20 may also retrieve usage information, e.g., information relating to the extent or times of use for one or more programs that were sent home with the patient after a previous programming session, and may update the record for those programs within the programming history to include the usage information. Clinician programmer 20 may also retrieve patient diary information associated with the one or more programs, which may include subject comments regarding efficacy, side-effects, use, or the like, recorded by patient 12 during use of the programs, e.g., outside of the clinic setting. Usage information and patient diary information may be stored by, and therefore retrieved from, one or both of IMD 14 and patient programmer 26.

Clinician programmer 20 may display the programming history to the clinician during the current programming session via display 22, and the display of the programming history may assist the clinician in more quickly identifying desirable programs during the current programming session. Clinician programmer 20 may receive selection of a particular field within the programming history, e.g., effectiveness or side effects, via display 22, keypad 24, or a pointing device, and may order the programming history according to the selected field. Further, as will be described in greater detail below, clinician programmer 20 may analyze, or otherwise use the programming history to provide guidance information to a user, such as a clinician, via display 20. The guidance information may assist the user in more quickly identifying one or more desirable programs during the current programming session.

In addition to maintaining a programming history for patient 12, clinician programmer 20 may also store some or all of the session logs for the patient in one or more of a fixed or removable memory of the clinician programmer, patient programmer 26, IMD 14, or a memory of another computing device coupled to the clinician programmer, e.g., via a network. When not stored within clinician programmer 20, the clinician programmer may retrieve the historical session logs for use during a current programming session.

In some embodiments, as discussed above, the clinician programmer only includes selected programs from each of the session logs in the programming history. For example, the programming history may include only information regarding programs that were in fact programmed into IMD 14 for long-term delivery of therapy at the end of a programming session, rather than all of the programs tested during the programming session. In this respect, the programming history may act as a summary of the various session logs. In some embodiments, in addition to accessing the programming history, the clinician programmer may access the historical session logs for information regarding programs or specific electrodes not included in the programming history to provide guidance information that may assist the user in more quickly identifying one or more desirable programs during the current programming session. In some embodiments, whether the information regarding a program or electrode is stored in a programming history or a historical session log, clinician programmer 20 may be able to access such information to provide guidance information to a user.

Figure 2:
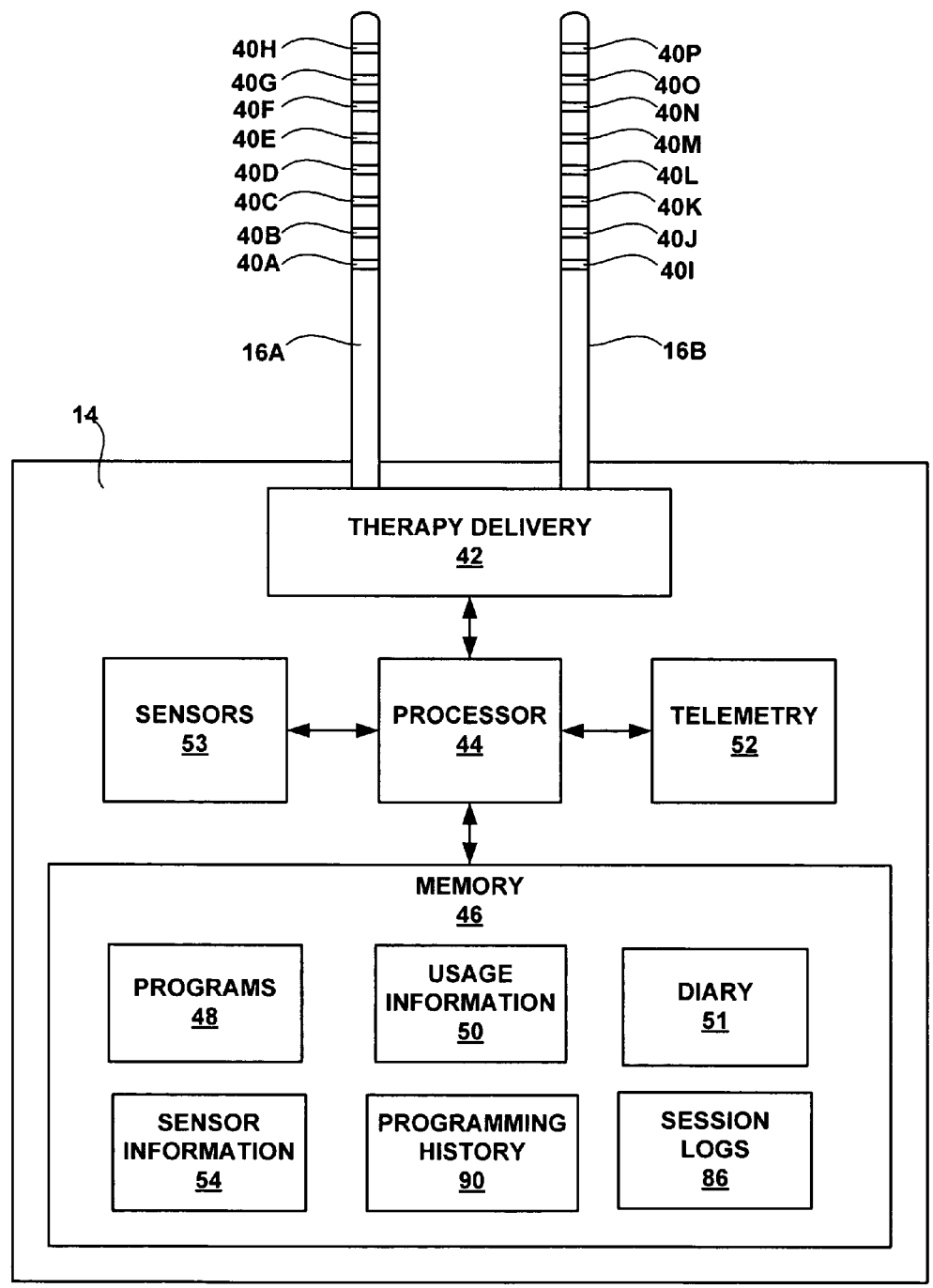
FIG. 2 is a block diagram illustrating an example implantable medical device for delivering therapy to a patient according to one or more programs.

FIG. 2 is a block diagram illustrating an example configuration of IMD 14. IMD 14 may deliver neurostimulation therapy via electrodes 40A-H of lead 16A and electrodes 40I-P of lead 16B (collectively "electrodes 40"). Electrodes 40 may be ring electrodes. The configuration, type and number of electrodes 40 illustrated in FIG. 2 are merely exemplary.

Electrodes 40 are electrically coupled to a therapy delivery circuit 42 via leads 16. Therapy delivery circuit 42 may, for example, include an output pulse generator coupled to a power source such as a battery. Therapy delivery circuit 42 may deliver electrical pulses to patient 12 via at least some of electrodes 40 under the control of a processor 44.

Processor 44 controls therapy delivery circuit 42 to deliver neurostimulation therapy according to one or more selected programs. Specifically, processor 44 may control circuit 42 to deliver electrical pulses with the amplitudes and widths, and at the rates specified by the one or more selected programs. Processor 44 may also control circuit 42 to deliver the pulses via a selected subset of electrodes 40 with selected polarities, as specified by the selected programs. Where a plurality of programs are selected at a given time, processor 44 may control circuit 42 to deliver each pulse according to a different one of the selected programs. Processor 44 may include a microprocessor, a controller, a digital signal processor (DSP), an application specific integrated circuit (ASIC), a field programmable gate array (FPGA), or other discrete or integrated logic circuitry.

IMD 14 also includes a memory 46. In some embodiments, memory 46 may store programs 48 that are available to be selected by patient 12 for delivery of neurostimulation therapy. In some embodiments, processor 44 may record usage information 50, and store usage information 50 in memory 46. Memory 46 may also include program instructions that, when executed by processor 44, cause processor 44 and IMD 14 to perform the functions ascribed to IMD 14 herein. Memory 46 may include any volatile, non-volatile, fixed, removable, magnetic, optical, or electrical media, such as a RAM, ROM, NVRAM, EEPROM, flash memory, and the like.

IMD 14 also includes a telemetry circuit 52 that allows processor 44 to communicate with clinician programmer 20 and patient programmer 26. Processor 44 may receive programs to test on patient 12 from clinician programmer 20 via telemetry circuit 52 during a programming session. Where IMD 14 stores programs 48 in memory 46 for long-term use, processor 44 may receive programs 48 from clinician programmer 20 via telemetry circuit 52, e.g., at the end of a programming session, and later receive program selections made by patient 12 from patient programmer 26 via telemetry circuit 52. Where patient programmer 26 stores the programs, processor 44 may receive programs selected by patient 12 from patient programmer 26 via telemetry circuit 52.

In some embodiments, processor 44 receives patient diary information 51 entered by patient 12 using patient programmer 26 via telemetry circuit 52, and stores the diary information within memory 46. Clinician programmer 20 may retrieve usage information 50 and diary information 51 from memory 46 via telemetry circuit 52.

Further, in some embodiments, as discussed above, clinician programmer 20 stores a programming history 90 and session logs 86 within memory 46 of IMD 14, and retrieves the programming history and session logs from memory 46, via telemetry circuit 52. The clinician programmer may retrieve and update the programming history and session logs during each new session. Maintaining the programming history and session logs within memory 46 of IMD 14 may be advantageous in situations where patient 12 may visit a different clinic or, in any event, where IMD 14 may communicate with different clinician programmers 20. In such cases, the programming history 90 and session logs 86 are stored with patient 12 and available to all such clinics, clinicians, or clinician programmers.

Additionally, as illustrated in FIG. 2, IMD 14 may include one or more physiological sensors 53 that generate signals as a function of a physiological parameter of patient 12. For example, physiological sensors 53 may include accelerometers or other sensors that generate signals as a function of patient activity, gait or posture. As other examples, physiological sensors 53 may include electrodes that detect an electromyogram (EMG), electrocardiogram (ECG), electroencephalogram (EEG), or impedance-based respiration of patient 12. Further, physiological sensors 53 may include known transducers that generate a signal based on a blood pressure or blood oxygen saturation of patient 12. Although illustrated in FIG. 2 as being located within IMD 14, sensors 53 may additionally or alternatively be coupled to IMD 14 wirelessly or via leads.

Processor 44 may store sensor information 54 in memory 46 based on the signals generated by sensors 53. The physiological parameters detected by sensors 53 and, therefore, sensor information 54, may reflect the severity or prevalence of pain, movement disorders, epilepsy, mood disorders, cardiac disorders, gastrointestinal or urinary disorders, or side-effects associated with the treatment of such symptoms or disorders. In some embodiments, processor 44 may associate sensor information 54 with the one or more of programs 48 presently used by therapy delivery circuitry 42 for delivery of therapy, e.g., neurostimulation patient 12. In this manner, sensor information 54 may advantageously provide objective information regarding the efficacy or side-effects associated with delivery of therapy according to the programs. In some embodiments, processor 44 may store sensor information 54 in association with the programs within the programming history 90, or may provide the sensor information to clinician programmer 20 for inclusion in a programming history and use in providing programming guidance.

Sensor information 54 may include raw data derived from the signals output by the sensors, averages or other statistical representations such data, or any other metric derived from such data. For example, in embodiments in which sensors 53 include one or more accelerometers or EMG electrodes, processor 44 may periodically detect the severity of tremor, or may detect incidences where patient 12 falls or experiences immobility, e.g., a gait freeze. Processor 44 may record the information describing the severity of the tremor and times of detection, or numbers and times of falls or immobility, as sensor information 54. These examples of sensor information 54 may be particularly relevant as, for example, an objective indication of the efficacy of a movement disorder treatment program, e.g., a deep brain stimulation program.

In addition to the specific examples discussed above, sensors 53 may include any of the sensors, and sensor information 54 may include any of the activity, posture, sleep quality, or other metrics described in the following U.S. Patent Applications, each of which is incorporated herein by reference in its entirety: U.S. patent application Ser. No. 11/081,811, entitled "COLLECTING SLEEP QUALITY INFORMATION VIA A MEDICAL DEVICE," filed on Mar. 16, 2005; U.S. patent application Ser. No. 11/081,872, entitled "COLLECTING POSTURE INFORMATION TO EVALUATE THERAPY," filed on Mar. 16, 2005; U.S. patent application Ser. No. 11/081,786, entitled "DETECTING SLEEP," filed on Mar. 16, 2005; U.S. patent application Ser. No. 11/081,785, entitled "COLLECTING ACTIVITY INFORMATION TO EVALUATE THERAPY," filed on Mar. 16, 2005; U.S. patent application Ser. No. 11/081,857, entitled "COLLECTING ACTIVITY AND SLEEP QUALITY INFORMATION VIA A MEDICAL DEVICE," filed on Mar. 16, 2005; U.S. patent application Ser. No. 11/081,155, entitled "CONTROLLING THERAPY BASED ON SLEEP QUALITY," filed on Mar. 16, 2005; and U.S. patent application Ser. No. 11/106,051, entitled "COLLECTING POSTURE AND ACTIVITY INFORMATION TO EVALUATE THERAPY," filed on Apr. 14, 2005.

Figure 3:
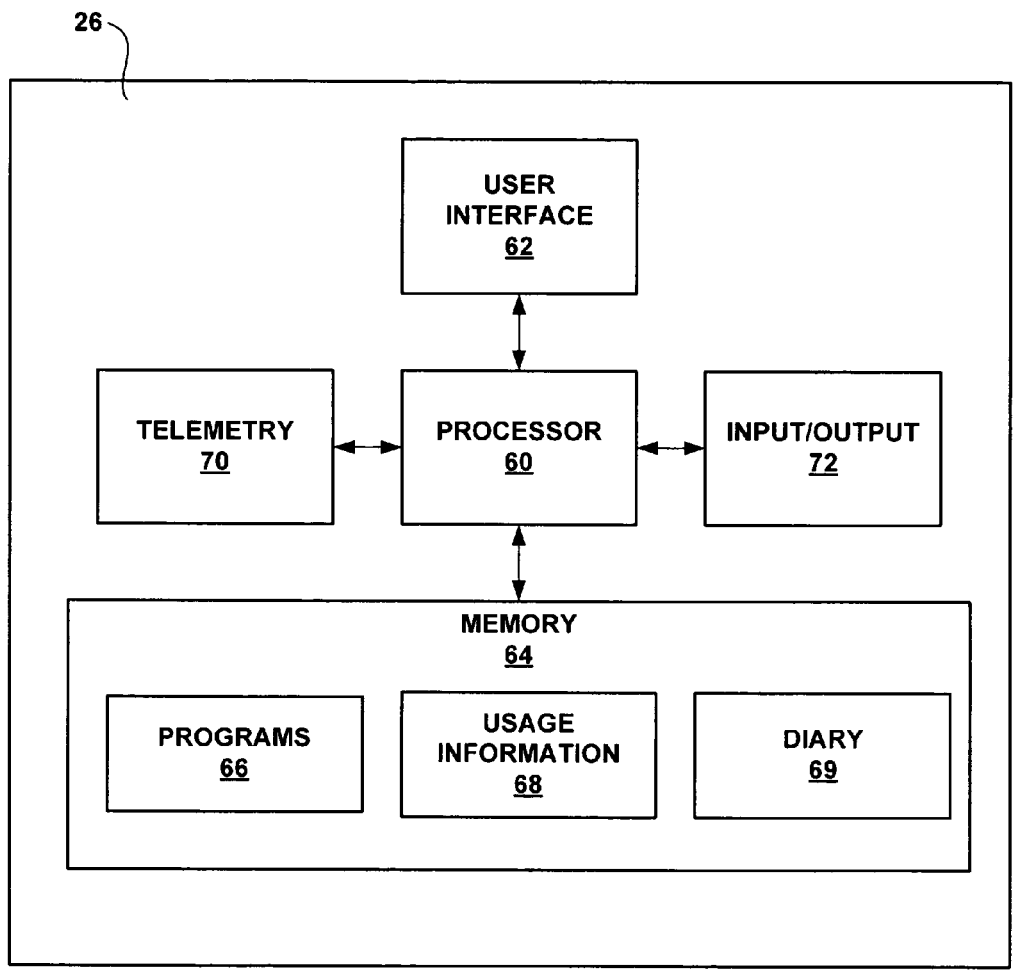
FIG. 3 is a block diagram illustrating an example patient programmer that allows a patient to control delivery of therapy by an implantable medical device.

FIG. 3 is a block diagram illustrating an example configuration of patient programmer 26. Patient 12 may interact with a processor 60 via a user interface 62 in order to control delivery of neurostimulation therapy as described herein. User interface 62 may include display 28 and keypad 30, and may also include a touch screen or peripheral pointing devices as described above. Processor 60 may also provide a graphical user interface (GUI) to facilitate interaction with patient 12, as will be described in greater detail below. Processor 60 may include a microprocessor, a controller, a DSP, an ASIC, an FPGA, discrete logic circuitry, or the like.

Patient programmer 26 also includes a memory 64. In some embodiments, memory 64 may store programs 66 that are available to be selected by patient 12 for delivery of neurostimulation therapy. In some embodiments, processor 60 may record usage information 68, and diary information 69 entered by patient 12 via user interface 62. Processor 60 stores the usage and diary information in memory 64.

Usage information 68 for a program may indicate, as examples, the number of times patient 12 selected a program, the average or median length of time that a program was used when selected, the average amount of time a program was used over a period of time, such as on a per day, week or month basis, or the total amount of time or percentage of time that the program was used since the most recent programming session. Diary information 69 may include, for example, textual or numerical comments or ratings entered by a patient for a program, which may be related to, for example, the efficacy or side-effects resulting from delivery of neurostimulation according to the program. Processor 60 may associate diary information 69 with the one or more of programs 66 to which it pertains, e.g., the programs according to which therapy was delivered when the diary information was collected. In this manner, diary 69 may provide a subjective indication of the efficacy or side effects associated with delivery of therapy according to a program.

In some embodiments, processor 60 may prompt patient 12 to enter diary information 69 for a program. Further, in some embodiments, the prompting by processor 60 may include questions intended elicit responses from the patient relating to efficacy or side effects of the program, or other metrics of the quality of the patient's life during delivery of the program. For example, processor 60 may ask patient 12 to indicate the severity of pain, or how often patient 12 has fallen or experienced immobility, during delivery of therapy according to a program. Such information in a diary 69 may provide a subjective indication of the efficacy or side effects associated with a pain or movement disorder therapy program, e.g., a spinal cord or deep brain stimulation program.

Memory 64 may also include program instructions that, when executed by processor 60, cause patient programmer 26 to perform the functions ascribed to patient programmer 26 herein. Memory 64 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Patient programmer 26 also includes a telemetry circuit 70 that allows processor 60 to communicate with IMD 14, and input/output circuitry 72 that to allow processor 60 to communicate with clinician programmer 20. Processor 60 may receive program selections made by patient 12 via user interface 62, and may transmit either the selection or the selected program to IMD 14 via telemetry circuitry 70 for delivery of neurostimulation therapy according to the selected program.

Where patient programmer 26 stores programs 66 in memory 64, processor 60 may receive programs 66 from clinician programmer 20 via input/output circuitry 72 that were selected for long-term use as a result of a programming session. Processor 60 may also provide usage information 68 and diary information 69 to clinician programmer 20 via circuitry 72. Circuitry 72 may include transceivers for wireless communication, appropriate ports for wired communication or communication via removable electrical media, or appropriate drives for communication via removable magnetic or optical media.

Further, although not illustrated in FIG. 3, in some embodiments, as described above, clinician programmer 20 may store programming history 90 and session logs 86 for patient 12 in memory 64 of patient programmer 26. Clinician programmer 20 may store, retrieve and update the programming history and session logs via telemetry circuitry 72. In some embodiments in which the programming history is stored in memory 64, processor 60 may update the programming history with usage information 68 and diary information 69 periodically or as such information is collected. In other embodiments, clinician programmer 20 may retrieve usage information 68 and diary information 69 from memory 64, and update the programming history based on such information.

Figure 4:
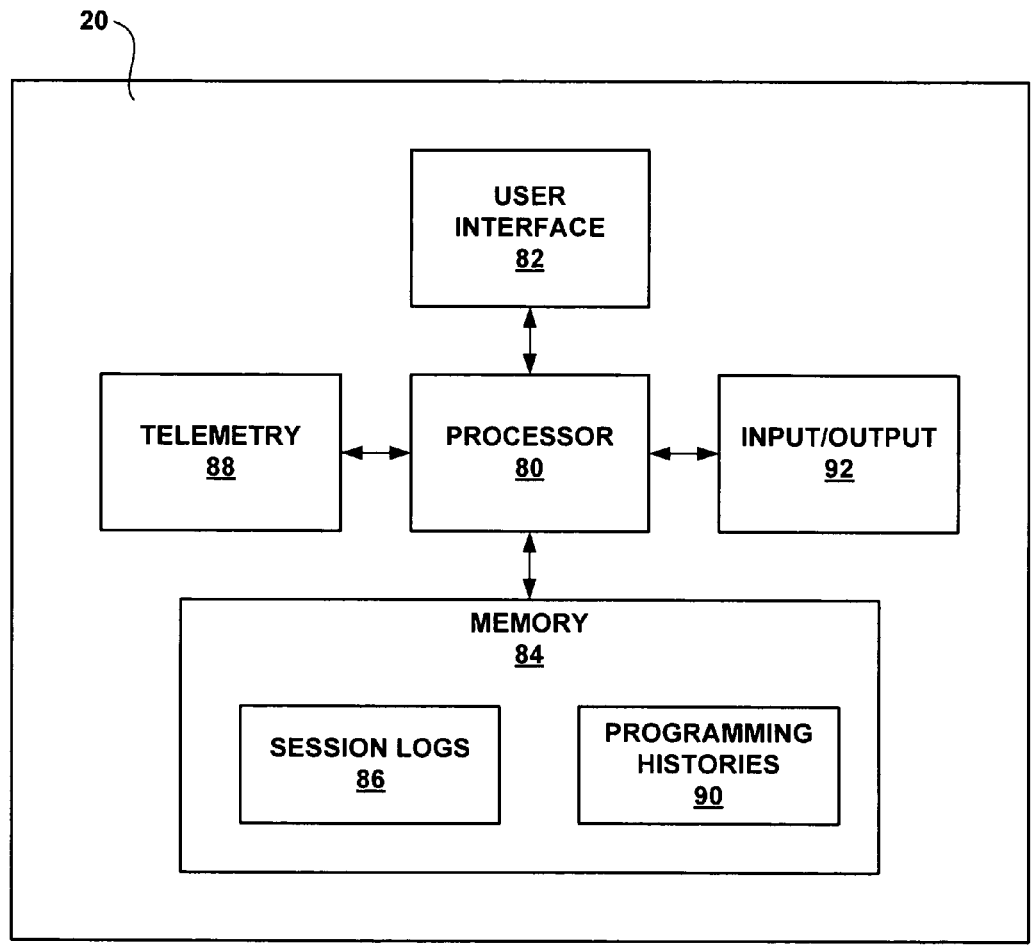
FIG. 4 is a block diagram illustrating an example clinician programmer that allows a clinician to program therapy for a patient by creating programs, and that maintains a programming history for the patient according to the invention.

FIG. 4 is a block diagram illustrating an example configuration of clinician programmer 20. A clinician may interact with a processor 80 via a user interface 82 in order to program neurostimulation therapy for patient 12 as described herein. User interface 82 may include display 22 and keypad 24, and may also include a touch screen or peripheral pointing devices as described above. Processor 80 may also provide a graphical user interface (GUI) to facilitate interaction with a clinician, as will be described in greater detail below. Processor 80 may include a microprocessor, a controller, a DSP, an ASIC, an FPGA, discrete logic circuitry, or the like.

Clinician programmer 20 also includes a memory 84. Memory 84 may include program instructions that, when executed by processor 80, cause clinician programmer 20 to perform the functions ascribed to clinician programmer 20 herein. Memory 84 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

A clinician may program neurostimulation therapy for patient 12 by specifying programs to test on patient 12. The clinician may interact with the GUI and user interface 82 in order to specify programs. Processor 80 transmits the selected or specified programs to IMD 14 for delivery to patient 12 via a telemetry circuit 88.

Processor 80 may maintain a session log 86 for patient 12 during programming of neurostimulation therapy for patient 12 by the clinician. Upon delivery of a selected or specified program, the clinician may receive feedback relating to the tested program from patient 12, and enter rating information relating to the tested program via the GUI and user interface 82. Processor 80 may store information identifying tested programs and associated rating information as part of session log 86. Information identifying tested programs may include the parameters for the tested programs. Processor 80 may present a listing of tested programs and associated rating information to the clinician in order to facilitate selection of programs for programming IMD 14. Session logs 86 may be stored in a volatile medium of memory 84, or may be stored within a non-volatile medium of memory 84, e.g. within a database of patient information.

Processor 80 may transmit programs created by the clinician to IMD 14 via telemetry circuitry 88, or to patient programmer 26 via input/output circuitry 92. In this manner, processor 80 may be used to control IMD 14 to deliver neurostimulation therapy for purposes of evaluating effectiveness of particular programs. I/O circuitry 92 may include transceivers for wireless communication, appropriate ports for wired communication or communication via removable electrical media, or appropriate drives for communication via removable magnetic or optical media.

Processor 80 may also maintain a programming history 90 for patient 12, which may take the form of a record of programs, e.g., combinations of therapy parameters tested during one or more prior programming sessions. During an initial programming session, processor 80 may create the programming history by storing all or selected ones of the programs within the session log 86 for that session within programming history 90. Similarly, processor 80 may include all or selected ones of the programs from the session logs 86 for follow-up programming sessions within the programming history 90 for patient 12, or may update the programming history 90 based on retesting of programs during a follow-up programming session. The programming history may include the information stored for a program in the session log 86, e.g., information describing the parameters and rating information for the program, and may include clinician comments regarding the program. The rating information may rate a program in terms of therapeutic efficacy, side effects, IMD power consumption associated with delivery of therapy according to the program, or the like.

In some embodiments, during a current programming session, processor 80 may retrieve usage information 50, 68, diary information 51, 69 and sensor information 54 from IMD 14 or patient programmer 26, and may update the record for those programs within the programming history 90 to include the usage, diary and sensor information. Processor 80 may display the programming history 90 to the clinician during the current programming session via the GUI provided by user interface 82, and the display of programming history 90 may assist the clinician in more quickly identifying desirable programs during the current programming session. Processor 80 may receive selection of a particular field within the programming history 90, e.g., rating information related to effectiveness or side effects, via user interface 82, and may order the display of the programming history 90 via the GUI according to the selected field. Further, as will be described in greater detail below, processor 80 may analyze, or otherwise use the programming history 90 to provide guidance information to a user, such as a clinician, via user interface 82. The guidance information may assist the user in more quickly identifying one or more desirable programs during the current programming session. Additionally, in embodiments in which the programming history 90 and session logs 86 for patient 12 include different information or different quantities of information, clinician programmer 20 may access historical session logs 86 as necessary during a programming session for presentation to a clinician or formulation of guidance information.

Although illustrated in FIG. 4 as stored within memory 84 that is within clinician programmer 20, programming histories 90 need not be stored within a fixed memory of the clinician programmer. Memory 84 may include removable media on which programming histories 90 may be stored, or programming histories 90 may be stored within a memory of another computing device accessible to processor 80, e.g., via a network. Further, processor 80 may store the programming histories for patient 12 within memory 46 of IMD 14 or memory 64 of patient programmer 26, and may retrieve the programming history during a current programming session for use during the programming session.

Figure 5:
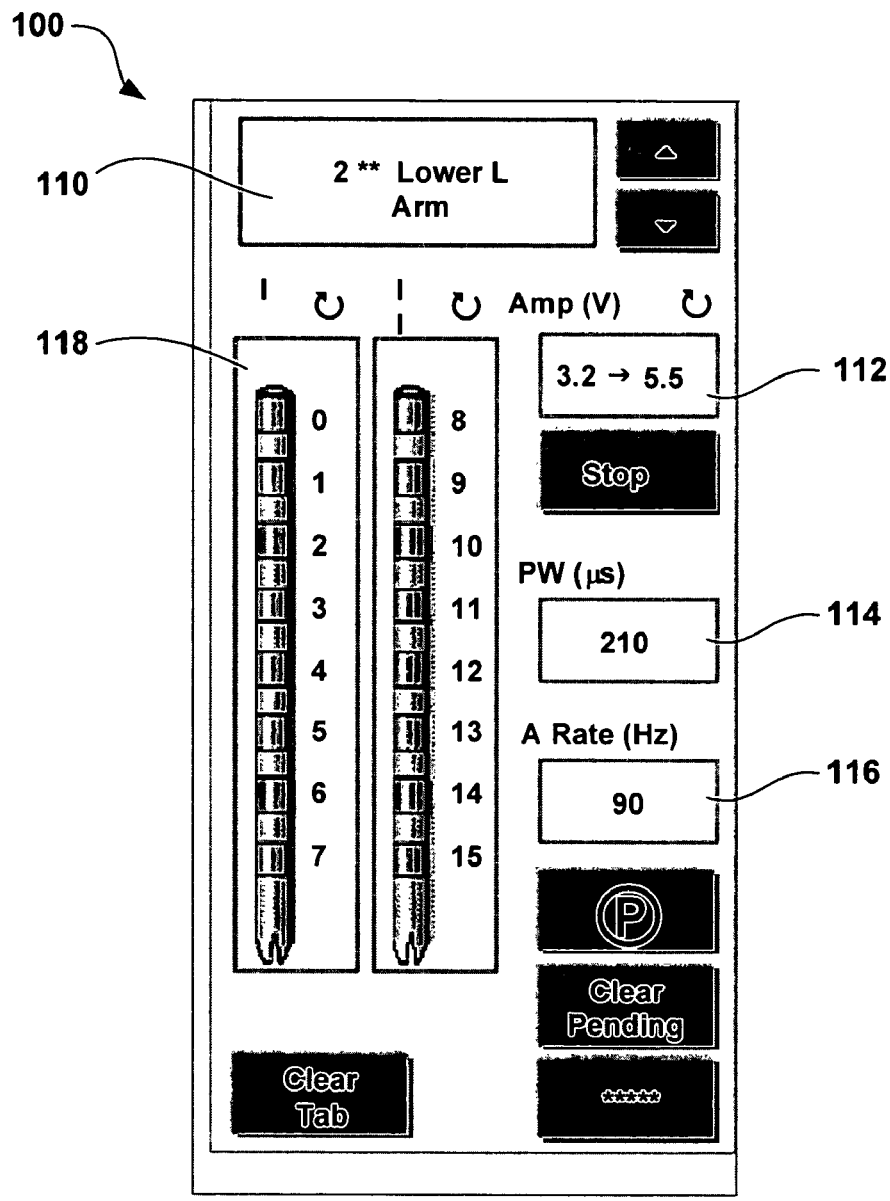
FIGS. 5-7 are conceptual diagrams illustrating an example graphical user interface that may be provided by a clinician programmer to allow a clinician to program neurostimulation therapy using a session log.
Figure 6:
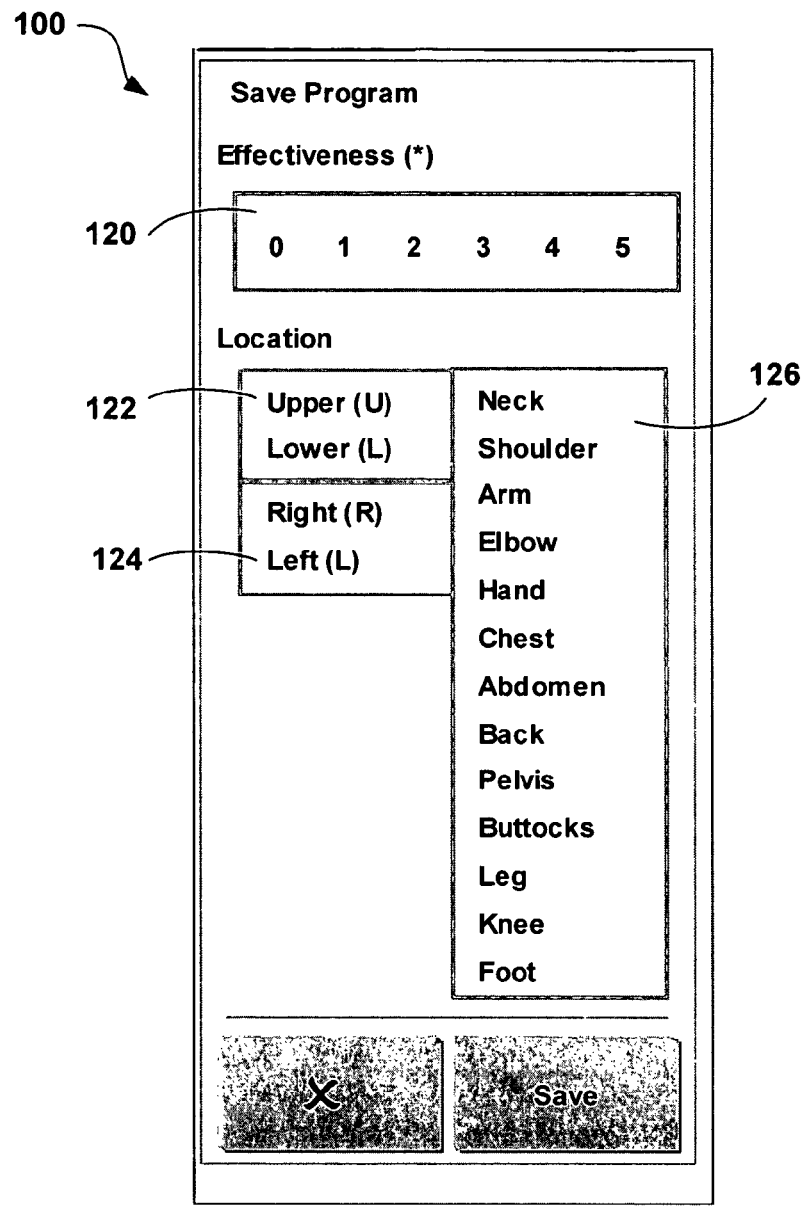
Figure 7:
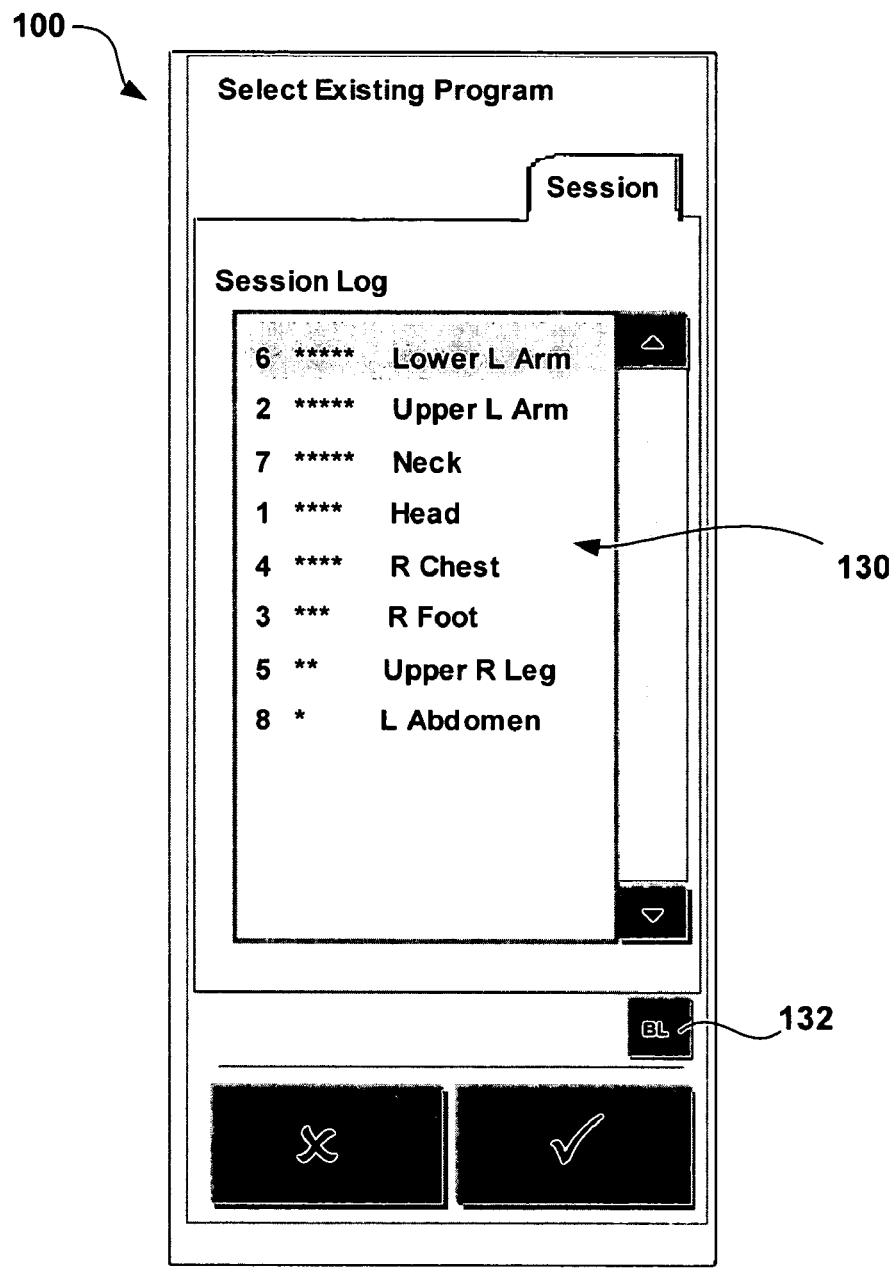

FIG. 5-7 are conceptual diagrams illustrating an example graphical user interface (GUI) 100 that may be provided by clinician programmer 20 to allow a clinician to program neurostimulation therapy for patient 12 using a session log 86. The configuration of GUI 100 illustrated in FIG. 5-7 is merely exemplary and is provided for purposes of illustration.

FIG. 5 illustrates a portion of GUI 100 that may be used by a clinician to specify a new program to test on patient 12. GUI 100 may, as shown in FIG. 5, include a field 110 which the clinician may use to name a new program for the session log 86. GUI 100 also includes fields 112-116, which the clinician may use to program parameter values such as pulse amplitude, pulse width and pulse rate for the new program, and a field 118, which the clinician may use to select particular electrodes 40 and assign polarities of selected electrodes 40 for the program. In particular, the clinician may select individual electrodes, e.g., with a stylus, to identify electrodes to be included in an electrode combination, and also specify polarities for the electrodes. For example, clicking once on an electrode within field 118 may specify selection of the electrode with a positive polarity, clicking twice on an electrode may specify selection of the electrode with a negative polarity, and clicking three times on an electrode may specify de-selection of the electrode and removal of the electrode from the pertinent electrode set for the program.

FIG. 6 illustrates a portion of GUI 100 that may be used by a clinician to enter rating information for a program tested on patient 12. Rating information may include information relating to the degree of effectiveness of the tested program in treating symptoms of patient 12 and the degree and/or types of side effects experienced by patient 12 due to the delivery of neurostimulation therapy according to the program. Effectiveness of a program may encompass both the coverage area provided by the program and degree of symptom relief. As an illustration, for spinal cord stimulation, symptom relief may be expressed in terms of overall pain relief on a numeric scale. Rating information may also, for example, include information relating to the performance of IMD 14 during delivery of neurostimulation according to the program.

Rating information may include information relating to at least one metric for rating the program, and may, as illustrated in FIG. 6, include numerical values. For example, as shown in FIG. 6, the clinician is prompted to enter a numerical rating for the effectiveness of the tested program using field 120. Multiple metrics may be used. For example, the clinician may provide a rating for the severity of side effects in general, for specific side effects, or for more particular measures of the effectiveness of a particular type of therapy. For example, different metrics may be applicable to pain, movement disorders, incontinence, sexual dysfunction, and gastrointestinal disorders. The clinician may select which of these types of metrics are to be used to evaluate tested programs.

Field 120 is merely exemplary, and numerical values for metrics may be entered using any type of field, such as a text box, drop-down menu, slider-bar, or the like. Moreover, rating information is not limited to numerical values, and may also, for example, include percentages or graphical or textual descriptions of the effectiveness, side-effects, and the like. An example of a graphic description is selection of one of a series of facial expressions representing a range between poor and good effectiveness, similar to pain scales used in many clinics. The clinician may use fields 122-126 to identify the location of the effectiveness of the tested program as reported by patient 12, and this location information may be used as a name for the tested program within session log 86.

Further, rating information can include a visual analog scale (VAS) rating for the program, entered by the clinician or patient 12 by, for example, moving a slider bar along a visual analog scale from 1 to 100 as provided by GUI 100. In some embodiments, GUI 100 may provide an outline or image of a human body, and the clinician or patient may indicate areas of pain, and areas of paresthesia for each program, on the body image. The paresthesia map and/or or a calculation of overlap between the indicated pain and paresthesia regions may be stored as rating information.

Figure 8:
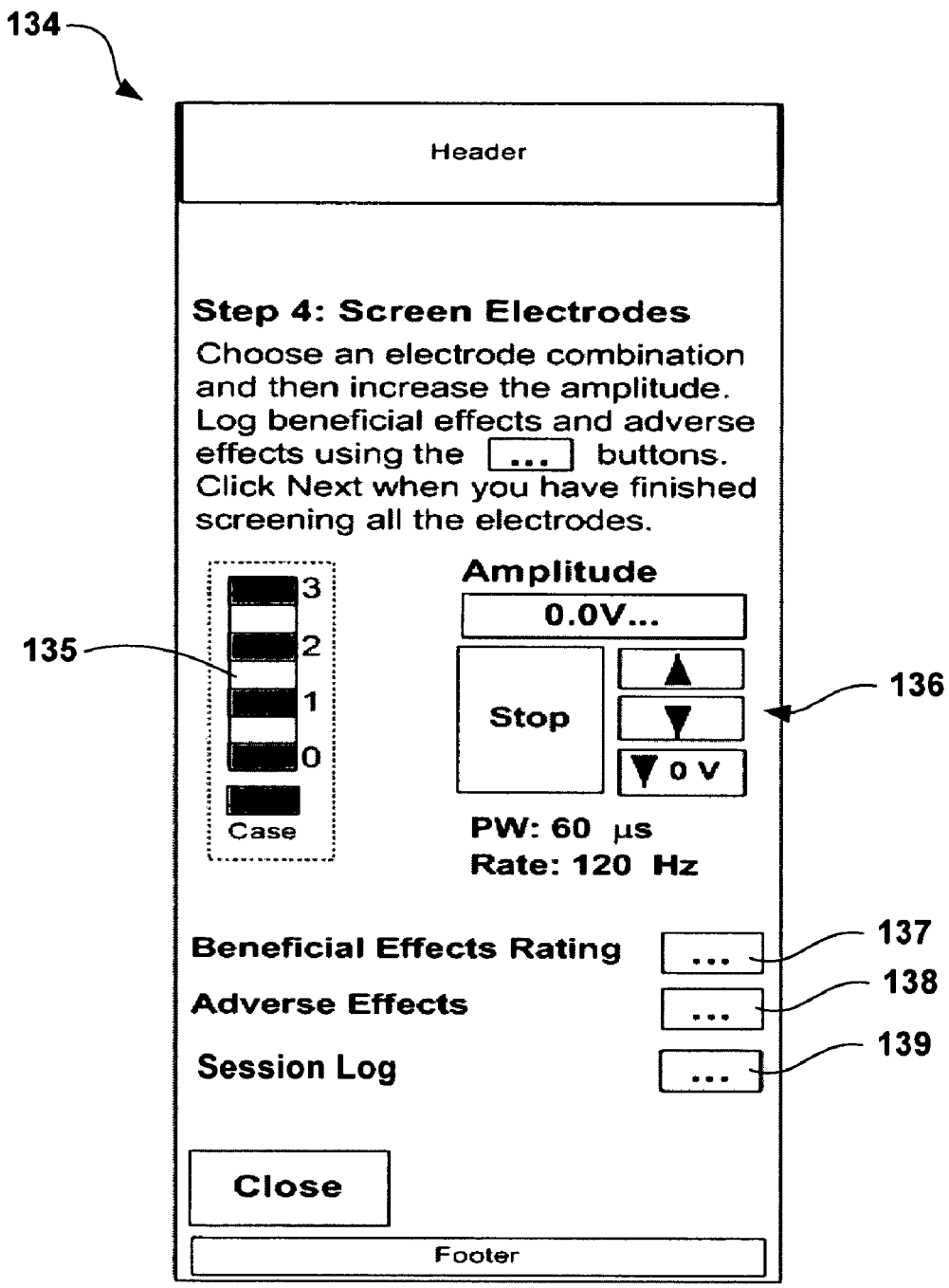
FIG. 8 is a conceptual diagram illustrating another example graphical user interface that may be provided by a clinician programmer to allow a clinician to program neurostimulation therapy using a session log.

FIG. 7 illustrates a portion of GUI 100 that may be used by clinician programmer 20 to present a list 130 of the programs identified within session log 86 and associated rating information. As shown in FIG. 8, list 130 may be ordered according to the rating information. In embodiments where more than one metric is used to rate programs, list 130 may be ordered according to a metric selected by the clinician, or an overall rating may be calculated based on a number of metrics, and the list may be ordered according to the overall rating. For an overall rating, weighting factors, which may be selected by the clinician, may be applied to the metrics.

Ordering of list 130 according to rating information may facilitate comparison of the programs and quick program selection by the clinician. The clinician may select a program from list 130 for inclusion in programs based on the rating information. List 130 may also facilitate retransmission of multiple programs from list 130 to IMD 14 for side-by-side comparison, e.g., if multiple programs directed toward a particular symptom are closely rated. In such embodiments, clinician programmer 20 may prompt the clinician to add one of the compared programs to a parameter set, or remove one of the compared programs. In some embodiments, clinician programmer 20 may automatically select programs from session log 86 for inclusion in a parameter set based on the rating information.

Where a program or program parameter value is particularly ineffective, the clinician may "blacklist" the program or parameter value using field 132 ("BL") to indicate that the program is undesired. Clinician programmer 20 may store an indication that the program is blacklisted, i.e., undesired based on ineffectiveness or side effects within session log 86. Blacklisting of programs within session log 86 may allow the clinician to more easily avoid retrying particularly ineffective programs with patient 12, e.g., during reprogramming at a follow-up visit. Blacklisted programs within session log 86 may be removed from list 130, or identified within list 130 using highlighting, text effects, a symbol, or the like. In some embodiments, blacklisting field 132 may be provided within the portion of GUI 100 that may be used by a clinician to enter rating information for a program tested on patient 12

FIG. 8 is a conceptual diagram illustrating another example graphical user interface (GUI) 134 that may be provided by a clinician programmer 20 to allow a clinician to program neurostimulation therapy using a session log. Like GUI 100 described above with reference to FIG. 5-7, GUI 134 provides a field 135 that a clinician may use to select electrodes for a program to be tested on patient 12, as well as fields 136 that the clinician may use to select other parameters for the program, such as pulse rate, pulse width and amplitude. In the illustrated example, field 136 includes arrow-buttons that the clinician or patient may use to change the amplitude for a program. GUI 134 also provides buttons 137 and 138 that the clinician or patient may use to enter rating information side effect information. Selection of buttons 137 and 138 may cause text boxes or drop down menus, as examples, to appear, which the clinician or patient may use to enter or select rating information or side effects.

In some embodiments, the user may use the amplitude buttons of field 136 to increase amplitude for the program until beneficial or adverse, e.g., side, effects are first detected. The clinician or user may then select one of buttons 137 or 138 to enter rating or side effect information. The user may continue to increase amplitude, and select one of buttons 137 and 138 whenever the rating or side effects increase or otherwise change. When the user reaches an amplitude at which the negative effects of the stimulation are intolerable by patient 12, or the amplitude cannot be further increased, the user may select button 139. In response to selection of button 139, clinician programmer 20 may cause the program, including amplitude, rating and side effect information for the program, to be stored in session log 86.

In some embodiments, programmer 20 may store all amplitudes tested for a program in session log 86. In other embodiments, programmer 20 may store only the amplitudes at which efficacy or side effect rating information was entered or changed by the user, along with the rating information. Programmer 20 may store such information in session logs as ranges of amplitudes associated with a particular efficacy rating or side effect. For example, for a program stored in a session log, a range of 2.5-4.0 Volts may be associated with an efficacy rating of 4.5 on a numeric scale between 0.0 and 5.0, and a range of 3.5-5.0 Volts may be associated with a particular side effect, such as discomfort or speech difficulty. Programmer 20 may further reduce the amount of data stored within session log 86 for a particular program by, for example, only storing the amplitude at which the effects of the stimulation are first perceived by patient 12, the amplitude at which the best efficacy from the stimulation is experienced by patient 12, and the amplitude at which the side effects associated with stimulation is no longer tolerable.

In some embodiments, clinician programmer 20 may store an indication of a "therapeutic range,", e.g., the range from the amplitude of first effect perception to the amplitude at which side effects are intolerable, for each program in session log 86. The clinician programmer may store the therapeutic range as a range between the two end points, or as a value equal to the difference between the end points of the range. The therapeutic range may be a particularly useful indicator of the overall effectiveness of a program, because it indicates the extent to which patient 12 will be able to adjust amplitude to address changing symptom intensity, side effects, or therapy accommodation, without requiring selection of a new program, or an additional in-clinic programming session.

In some embodiments, to further reduce the amount of data stored within session log 86, programmer 20 may only store the therapy range for a program, rather than all amplitude points, or some larger subset of the amplitude points. Further, in addition to or instead of session logs 86, the clinician programmer may apply this or any of the other data reduction techniques discussed above to programs stored in programming history 90. Reducing the amount of data stored for each program in one or both of the session logs and programming history may be particularly beneficial in embodiments in which the clinician programmer 20 stores such data in IMD 14, which may include less memory than an external programmer.

Figure 9:
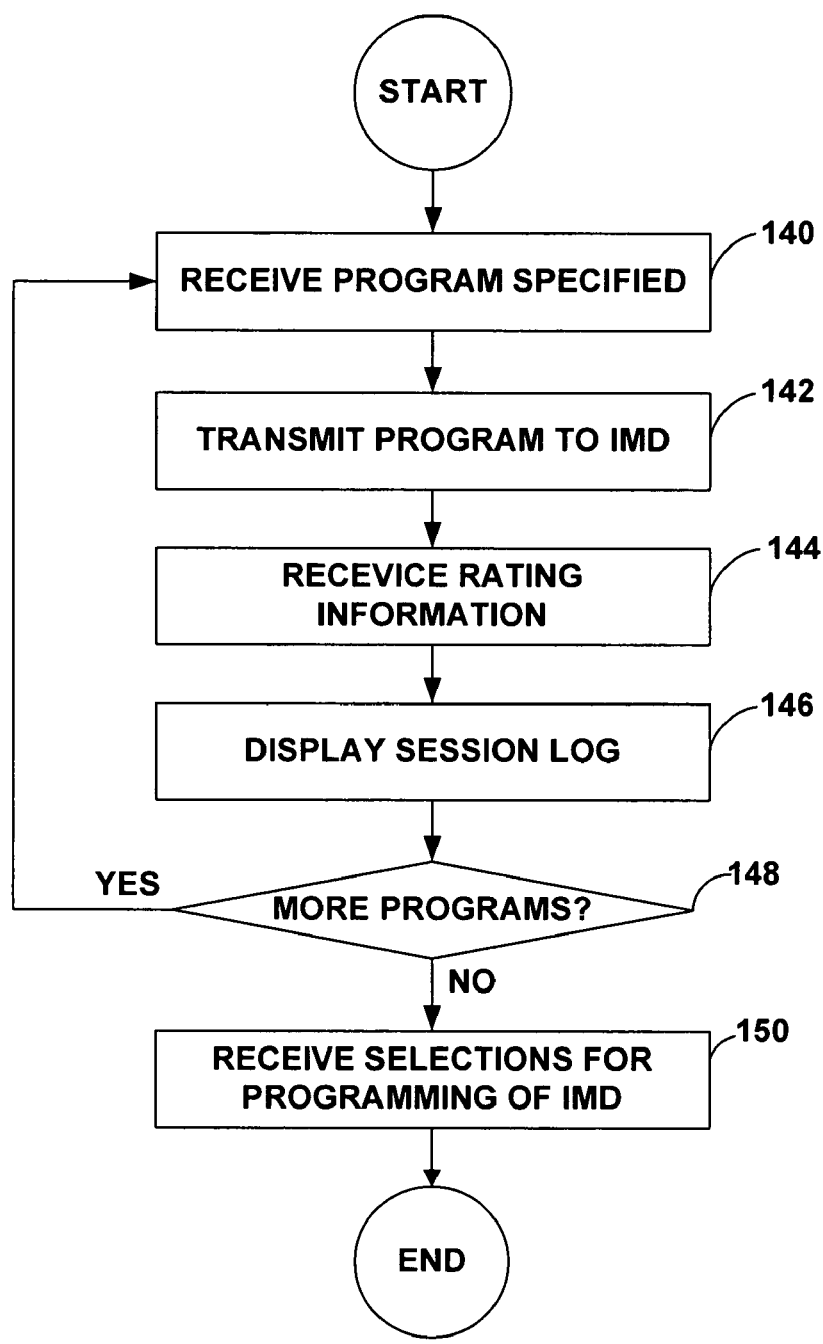
FIG. 9 is a flow diagram illustrating an example method that may be employed by a clinician programmer to allow a clinician to program neurostimulation therapy using a session log.

FIG. 9 is a flowchart illustrating a method that may be employed by clinician programmer 20 to allow a clinician to program neurostimulation therapy using session log 86. Clinician programmer 20 receives a program to test that is specified by the clinician (140), and transmits the program to IMD 14 to control delivery of neurostimulation therapy according to the program (142). The clinician receives feedback from patient 12, and records rating information, which may include information related to efficacy and/or side effects, as described above (144). Clinician programmer 20 displays a list 130 of programs and rating information from session log 86 (146), which may be ordered according to the rating information, and may update the list after each new program is tested (148). When the clinician has completed testing programs, clinician programmer 20 may receive selections from list 130 for creation of parameter sets (150).

Figure 10:
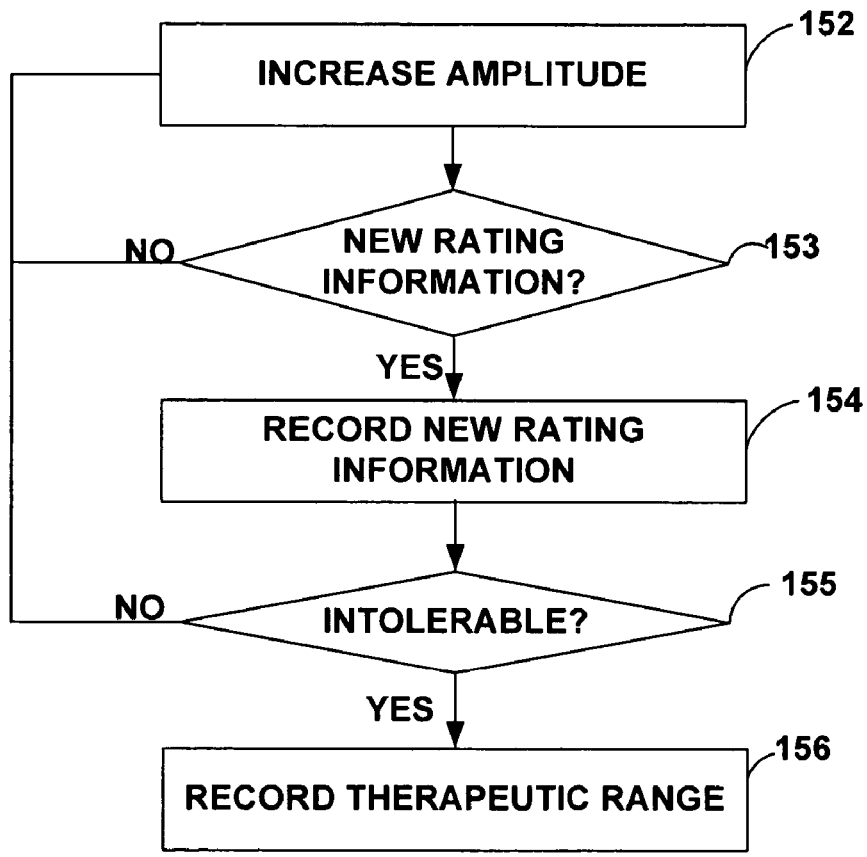
FIG. 10 is a flow diagram illustrating an example method for recording rating information for a session log during programming of neurostimulation therapy.

FIG. 10 is a flow diagram illustrating an example method for recording rating information for a session log during programming of neurostimulation therapy. In particular, FIG. 10 illustrates an example method in which particular stimulation amplitudes are identified, rating information is collected at the amplitudes, and a therapeutic range is identified. Although described with reference to amplitude for neurostimulation, the method of FIG. 10, including the recording of rating information at particular points and the identification of a therapeutic range, may be applicable to other therapies. For example, rating information may be recorded at particular points and a therapeutic range may be similarly identified during increases in the titration rate of a drug therapy.

According to the illustrated example method, clinician programmer 20 directs IMD 14 to increase the amplitude for a program as directed by a user, e.g., a clinician or patient 12 (152). The user may direct programmer 20 to increase the amplitude via one of GUIs 100 and 134 as described above. The user may increase the amplitude until the user first desires to record rating information for the program, e.g., until a beneficial effect resulting from delivery of stimulation according to the program is first perceived (153). The clinician programmer 20 may then record any of the types of rating information discusses above for the program, e.g., a numeric efficacy rating, based on input from the user (154).

The clinician programmer 20 may continue to increase amplitude (152), and record beneficial and side effect rating information (154) as directed by the user, until the user indicates that the stimulation has reached an amplitude such that the side effects are no longer tolerable by patient 12 (155). As discussed above, the user may direct the clinician programmer to record rating information whenever it changes, e.g. when the efficacy or side effects increase or decrease, or a new side effect is perceived. Clinician programmer 20 may also determine the therapeutic range for the program, e.g., based on the amplitudes at which beneficial effects are first perceived and at which stimulation is no longer tolerable (156).

FIG. 11A is a conceptual diagram illustrating display of an example stored programming history 90 by GUI 100 of clinician programmer 20. In particular, FIG. 9 illustrates display of the programming history 90 in the form of a list 160A of programs tested on patient 12 across one or more prior programming sessions. In the illustrated embodiment, list 160A displays information stored as part of the programming history 90, which includes a date tested, electrode configuration, pulse parameters, effectiveness related rating information, and side effect related rating information for each program.

Programming history 90 and list 160A further include an indication of whether patient 12 was sent home with the program at the end of the session in which it was tested, any usage information 50, 68 collected by IMD 14 or patient programmer 26 for each program, and any comments entered by the clinician for each program. Usage information may, as indicated in FIG. 9, include a percent or amount of time that the program was used, and may also indicate what times of day or timeframe within the period since the last programming session that the program was most frequently used. Although not illustrated in FIG. 9, programming history 90 and list 160A may include patient diary information, which may be in the form of textual comments regarding efficacy, side-effects, or use of a program, as well as other information regarding the quality of life experienced by patient 12 during use of the program, entered by a user using patient programmer 26. Further, programming history 90 and list 160A may include sensor information 54, such as various metrics of patient activity, as discussed above.

FIG. 11B is a conceptual diagram illustrating display of another example stored programming history 90 by GUI 134 in the form of a list 160B. In general, the programming history of FIG. 11B and list 160B include substantially similar information to the programming history and list 160A of FIG. 11A. List 160B includes different electrode configuration representations and side effects that list 160A, and also includes a therapy range for each program. While both of lists 160A and 160B may represent relevant programming history information for any type of neurostimulation, the electrode configurations and side effects in list 160A are generally associated with delivery of spinal cord stimulation to treat pain. The electrode configurations and side effects in list 160B, on the other hand, are generally associated with delivery of deep brain stimulation via one or more independent, hemispherical leads to treat, for example, a movement disorder.

Figure 12:
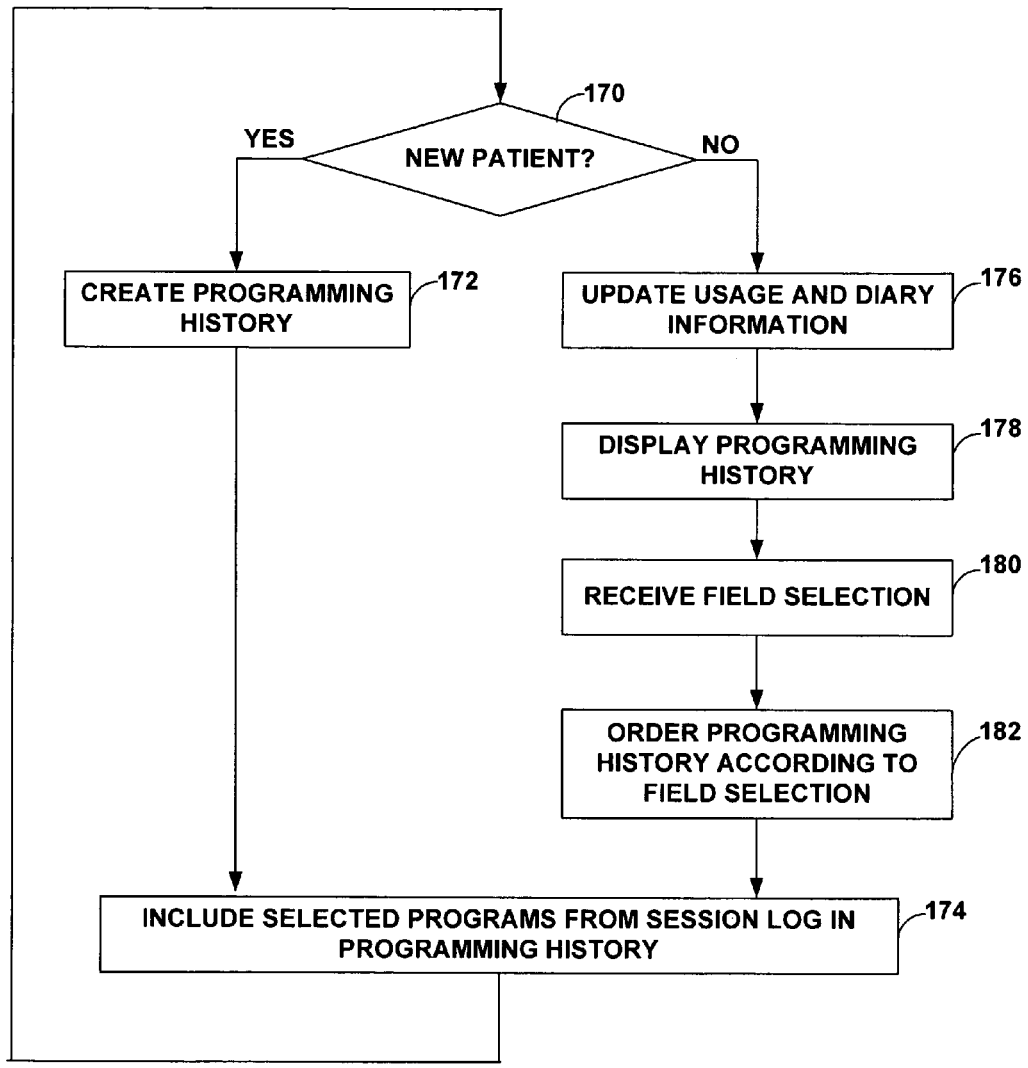
FIG. 12 is a flow diagram illustrating a method that may be employed by a clinician programmer to generate and update a programming history for a patient.

FIG. 12 is a flow diagram illustrating a method that may be employed by clinician programmer 20 to generate and update programming history 90 for patient 12. Clinician programmer 20 and, more particularly, processor 80 of clinician programmer 20 searches memory 84 to determine whether a programming history 90 has previously been created for patient 12 (170). If patient 12 is a new patient, clinician programmer 20 creates a new programming history 90 for patient 12 (172). Creation of a the programming history 90 may occur at the beginning, end, or any time during a programming session, which will generally be the initial programming session after implant of IMD 14 within patient 12.

As described above, clinician programmer 20 maintains a session log 86 for the current programming session that includes information describing the parameters, e.g., electrode configuration and pulse parameters, and rating information for each tested program. Clinician programmer 20 may create or update the programming history 90 by replicating the information included in the session log 86 to the programming history 90. Clinician programmer 20 may replicate records from the session log 86 to the programming history 90 automatically, based on individual selection by the clinician of programs, or based on some user configurable preference, such as "save all," "save none," "rating>X," "rating<Y." As another example, as described above, clinician programmer 20 may replicate only the records for programs selected for long term use in IMD 14 during a programming session from the session log to the programming history. The records relating to such programs may provide the most relevant information relating to the most efficacious programs to a clinician for review during future programming sessions.

If a programming history 90 was already created for patient 12 during a prior programming session, clinician programmer 20 may initially interrogate IMD 14 and patient programmer 26 for usage information 50, 68, diary information 51, 69, and sensor information 54, and may update the usage, diary and sensor information for one or more of the programs stored in the programming history 90 (176). As discussed above, in embodiments in which the programming history is stored in the IMD or patient programmer, the IMD or patient programmer may update the programming history with usage, diary or sensor information prior to transmitting the programming history to clinician programmer 20. Clinician programmer 20 may also display programming history 90 to the clinician to aid in the selection and testing of programs during the current programming session, e.g., display list 160 via GUI 100 (178). In some embodiments, clinician programmer 20 may receive a selection of one of the fields within the programming history 90 (180), e.g., effectiveness or side effects rating information, and may order list 160 according to the selected field (182). Ordering list 160 in this manner may allow the clinician to more easily identify relevant information about previously tested programs. Where a previously tested program is retested during the current programming session, clinician programmer 20 may update programming history 90 with newly collected information, e.g., rating information, for the retested program.

Figure 13:
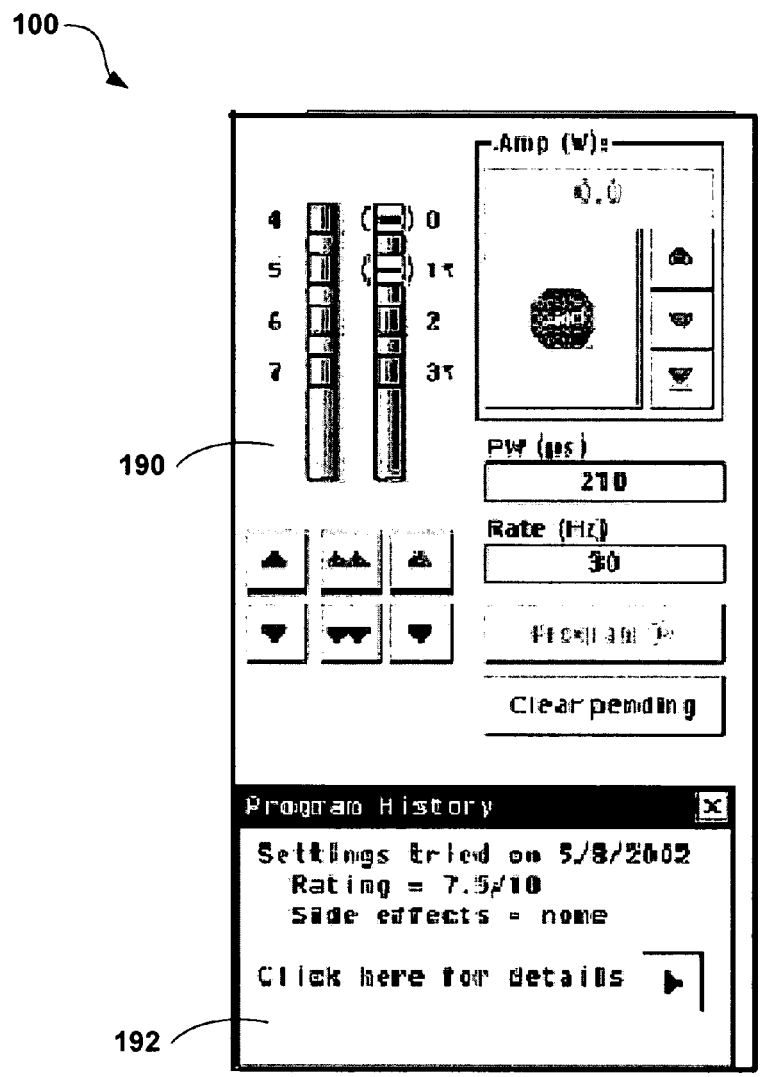
FIG. 13 is a conceptual diagram illustrating display of guidance information by an example graphical user interface of a clinician programmer based on comparison of program parameters to a stored programming history by the clinician programmer.

FIG. 13 is a conceptual diagram illustrating display of guidance information by example GUI 100 of clinician programmer 20 based on comparison of program parameters to a stored programming history 90 by clinician programmer 20. The illustrated portion of GUI 100 includes a parameter entry portion 190, which may correspond to the parameter entry portion of GUI 100 described with reference to FIG. 5. The illustrated portion of GUI 100 also includes a guidance information alert box 192.

Alert box 192 may be displayed by GUI 100 when, based on an analysis of the programming history 90, clinician programmer 20 identifies relevant guidance information that should be brought to the clinician's attention. In the illustrated example, alert box 192 indicates that new program fully or partially entered by the clinician matches or is similar to a previously tested program within the programming history 90. Clinician programmer 20 uses alert box 192 to bring the previously tested program, and its associated rating and usage information stored within programming history, to the attention of the clinician.

Figure 14:
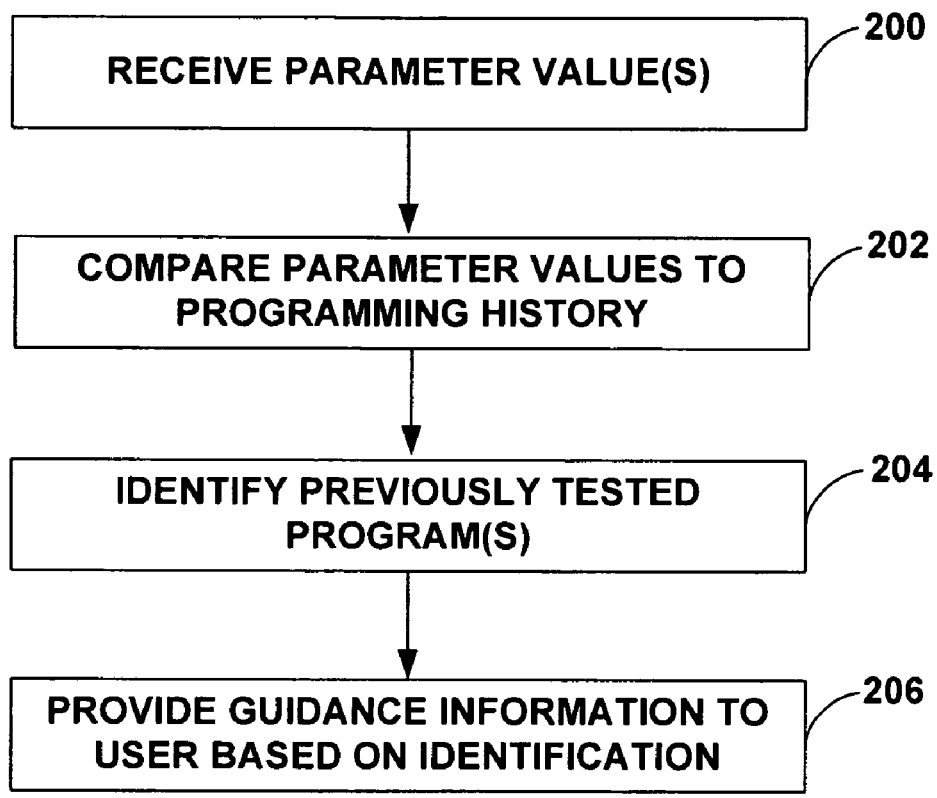
FIG. 14 is a flow diagram illustrating a method that may be employed by a clinician programmer to display guidance information based on comparison of program parameters to a stored programming history.

FIG. 14 is a flow diagram illustrating a method that may be employed by clinician programmer 20 to display guidance information based on comparison of program parameters to information stored within a programming history 90. Clinician programmer 20 receives a complete program or one or more parameters entered by the clinician via user interface 82, e.g., via parameter entry portion 190 of GUI 100, when the clinician attempts to create a new program for testing (200). Clinician programmer 20 compares the one or more parameters to information stored within the programming history 90, e.g., the parameters for previously tested programs stored in the program history 90 (202). Clinician programmer 20 identifies programs that have been previously tested that are the same or similar to the new program within the programming history 20 (204), and may bring the record of such programs within the programming history to the user's attention, e.g., display a message within alert box 192, as guidance information (206).

The clinician's decision of whether to proceed to test the program being entered may be informed by the results, e.g., rating and usage information, when the same or similar programs were previously tested. Further, when clinician programmer 20 identifies same or similar programs within the programming history 90 based on entry of only a portion of the parameters of a complete program, clinician programmer 20 may provide the parameters that would recreate one of the programs identified in the programming history based on the comparison to the clinician. In this manner, clinician programmer may act as a program generation "wizard," allowing the clinician to decide whether to test the automatically completed program, or to manually complete the program with different parameter values.

As another example, during a previous programming session, or during use by the patient outside of the clinic, a program, group of programs, or parameter value may have proven to be so ineffective or to have such undesirable side effects as to be "blacklisted" in a session log 86 and, consequently, within programming history 90. Blacklisting of programs or parameter values may be done automatically by clinician programmer 20 based on rating or usage information, or manually by the clinician. As an example, a particular electrode 40 on a lead 16 may have resulted in relatively severe side effects at relatively low amplitudes. In such cases, the electrode may be blacklisted, and clinician programmer may provide a warning when an electrode configuration including the electrode is selected.

Clinician programmer 20 may provide, for example, a visual indication such as highlighting or a text message within list 160 to indicate that the program or parameter value is blacklisted, and may also present such an indication during an attempt to create a program with the same or similar parameters during a current programming session. In some embodiments, clinician programmer 20 may "lock-out," e.g., prevent creation of programs with the same or similar parameter values as blacklisted parameter values, e.g., with an electrode configuration including a blacklisted electrode or adjacent electrodes, or the same or similar parameter values as a blacklisted program. As an example of blacklisting of a parameter value, a particular electrode 40 may be blacklisted due to undesirable side effects if, for example, it is located over a nerve root. Further, where a set of similar programs are blacklisted, clinician programmer 20 or clinician may determine that a particular value or range of values for one or more individual parameters should be blacklisted.

Figure 15:
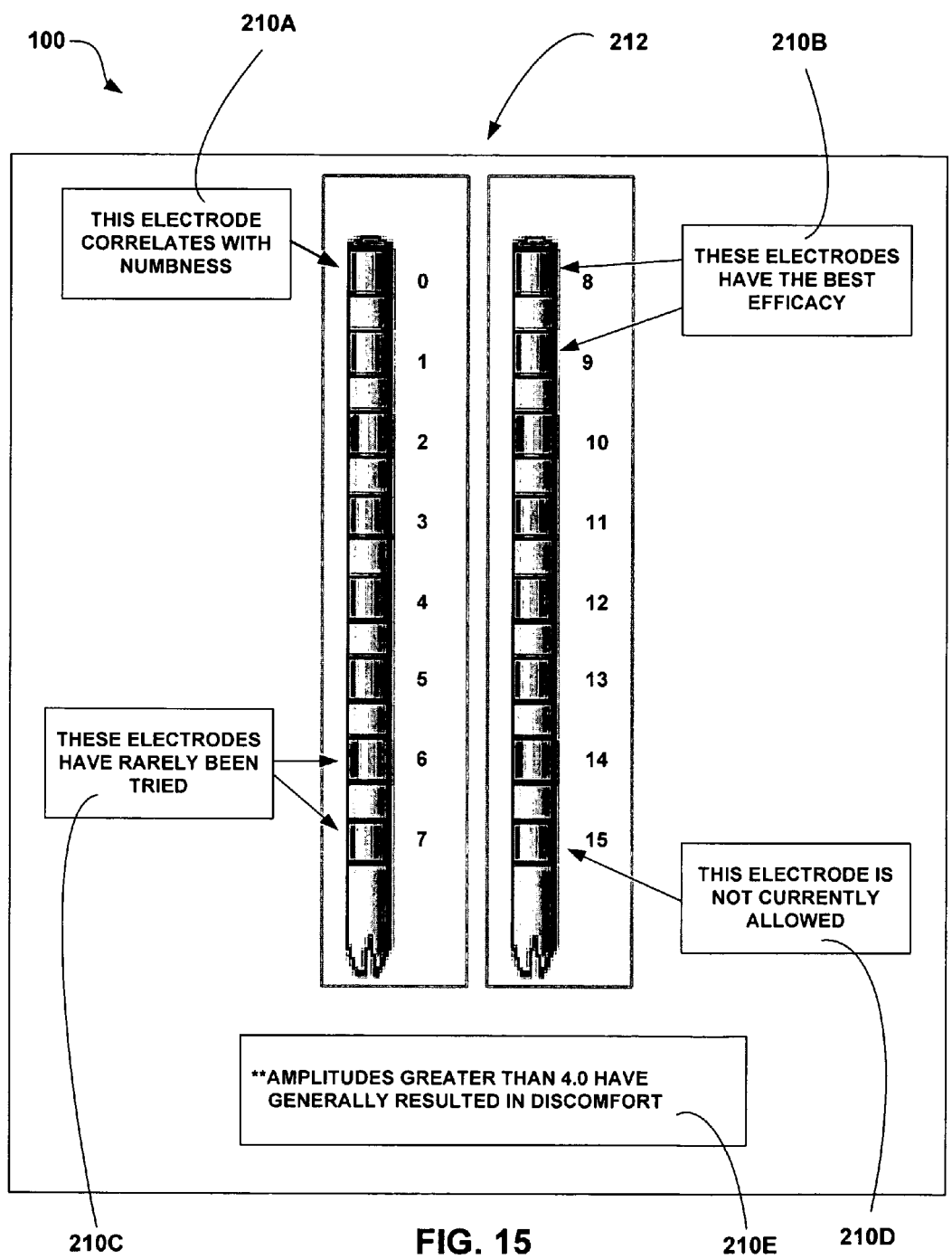
FIG. 15 is a conceptual diagram illustrating display of guidance information by an example graphical user interface of a clinician programmer based on analysis of a stored programming history by the clinician programmer.

FIG. 15 is a conceptual diagram illustrating display of guidance information by example GUI 100 of clinician programmer 20 based on analysis of a stored programming history 90 by clinician programmer 20. In the illustrated portion, GUI 100 presents a representation 212 of electrode set 16, and a variety of guidance information boxes 210A-E (collectively "guidance information boxes 210") through which clinician programmer presents guidance information to the clinician.

In particular, boxes 210A, B and E present the result of statistical or pattern analysis of programming history 90 to identify correlations between parameter values and rating information. Boxes 210A and B indicate that one or more electrodes are correlated with a particular side effect and high efficacy scores, respectively. Box 210E indicates that parameter values above an identified threshold are associated with a side effect. Box 210C indicates a result of analysis of programming history 90 to identify under tested parameter values, and specifically identifies electrodes that have been under-utilized. Box 210D indicates that an electrode has been blacklisted.

Although advantageous for any type of neurostimulation, the type of electrode specific information represented by Boxes 210A-D may be particularly advantages in embodiments in which deep brain stimulation is delivered to patient 12. In general, for deep brain stimulation, the correlation between electrodes and particular positive or negative effects is clear and can vary significantly from electrode to electrode. The increased correlation in the case of deep brain stimulation is based primarily on the different locations of the electrodes, which may be located in regions or structures of the brain that that result in vary different types of side effects or degrees of efficacy.

Figure 16:
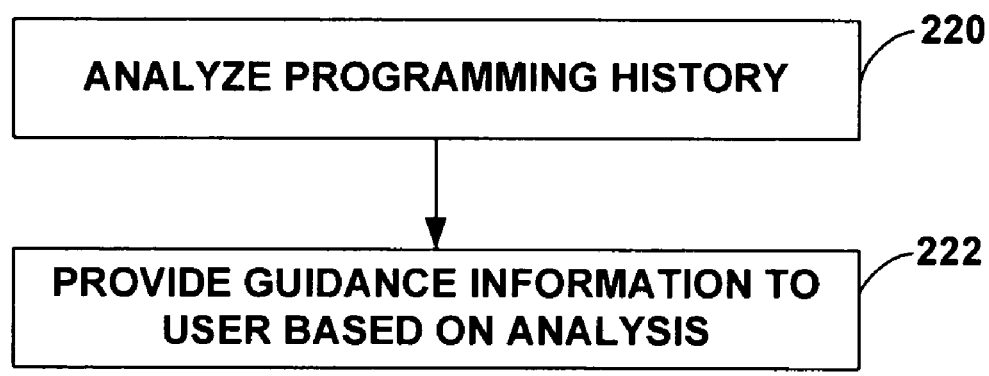
FIG. 16 is a flow diagram illustrating a method that may be employed by a clinician programmer to display guidance information based on an analysis of a stored programming history.
Figure 17:
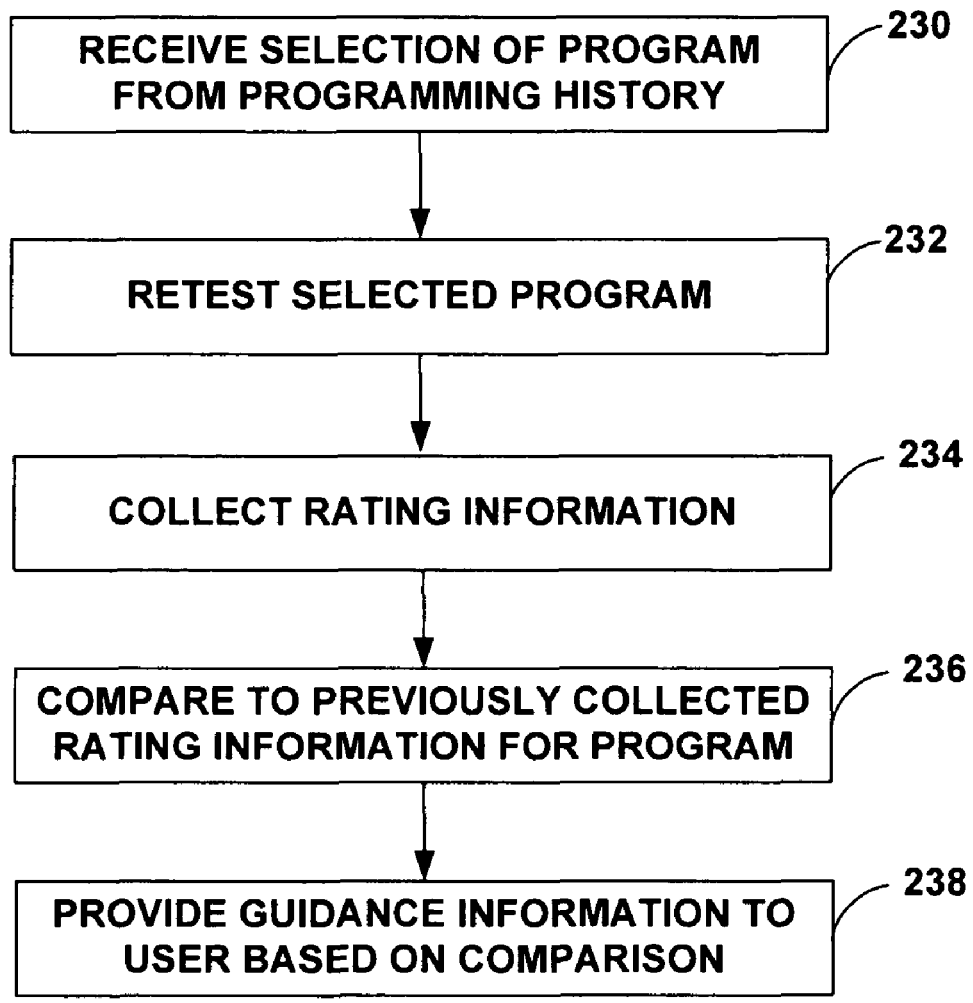
FIG. 17 is a flow diagram illustrating a method that may be employed by a clinician programmer to display guidance information based on a comparison of currently collected rating information for a program to previously collected rating information for the program that is stored within a programming history.

FIG. 16 is a flow diagram illustrating a method that may be employed by clinician programmer 20 to display guidance information based on an analysis of a stored programming history 90. According to the method, clinician programmer 20 analyzes the programming history (220), and provides guidance information to the clinician based on the analysis (222). For example, clinician programmer 20 may identify parameter values or ranges of parameter values that have not yet been tested or have not been frequently tested on patient 12, and can indicate these values or ranges to the clinician as illustrated in FIG. 13. The clinician may then choose to test programs that include under-tested parameter values or parameter value ranges.

Further, the clinician programmer 20 may perform a statistical or pattern matching analysis to correlate a parameter value or range of parameter values with rating information or usage information, e.g., an effectiveness or overall score, a particular side effect, or the amount of out of clinic use, and may provide guidance information to a user based on the results of the analysis. For example, clinician programmer may, as illustrated by boxes 210 of FIG. 13, indicate that particular parameter values or ranges have proven effective, or have proven to be correlated with a particular type of side effect or severity of side effects. In some embodiments, clinician programmer 20 may combine the identification of underutilized parameter values and such correlations to suggest untested programs, e.g., combinations of parameters, that may provide desirable efficacy and side effects as indicated by the correlations. Further, in embodiments in which clinician programmer 20 directs or suggests testing of parameter combinations according to a protocol, clinician programmer 20 may modify the protocol based on the correlations between parameter values or ranges and effectiveness or side effects to, for example, skip or add programs or parameter values.

FIG. 15 is a flow diagram illustrating a method that may be employed by clinician programmer 20 to display guidance information based on a comparison of currently collected rating information for a program to previously collected rating information for the program that is stored within a programming history. Clinician programmer 20 receives a selection of a previously tested program from the programming history 90 (230), and directs IMD 14 to retest the program (232). Clinician programmer 20 collects rating information based on the retesting of the program (234), and compares the currently collected rating information to rating information previously collected for the program that is stored in the programming history 90 (236). Clinician programmer 20 provides guidance information to the clinician based on the comparison (238). For example, if clinician programmer 20 identifies a significant change in the rating information over time, clinician programmer 20 may alert the clinician of the possibility of, for example, symptom or disease progression, or lead failure or movement. Additionally or alternatively, clinician programmer 20 may present trend charts or diagram of rating information for one or more programs over time, which the clinician may use to detect, for example, symptom or disease progression, or lead failure or movement.

Figure 18:
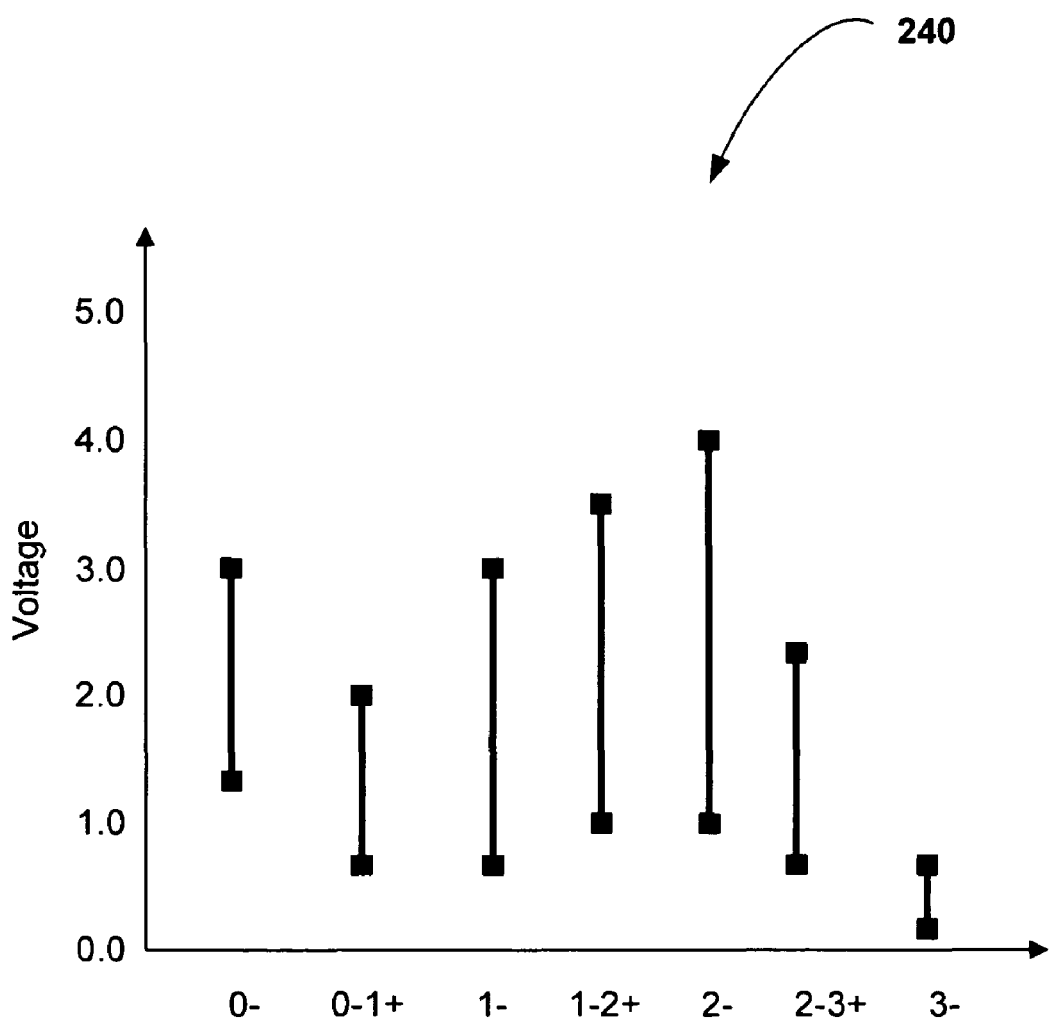
FIGS. 18-20 are conceptual diagrams illustrating examples of graphical guidance information that may be provided to a clinician by a clinician programmer based on a stored programming history.
Figure 19:
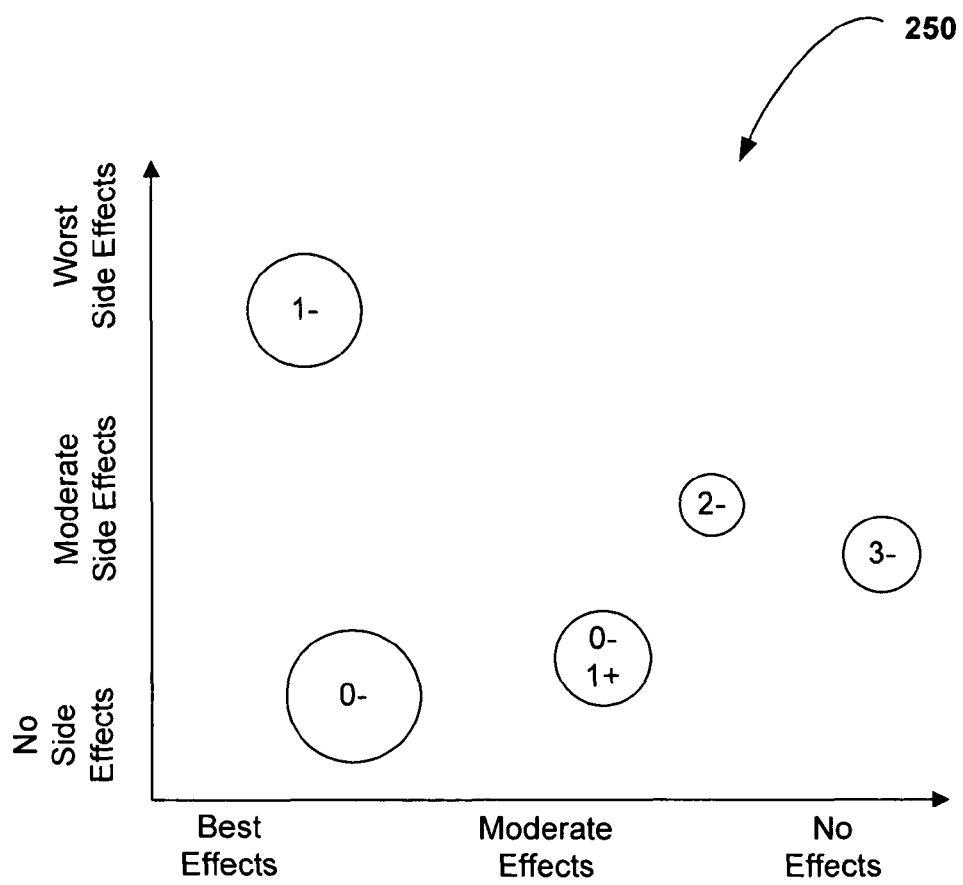
Figure 20:
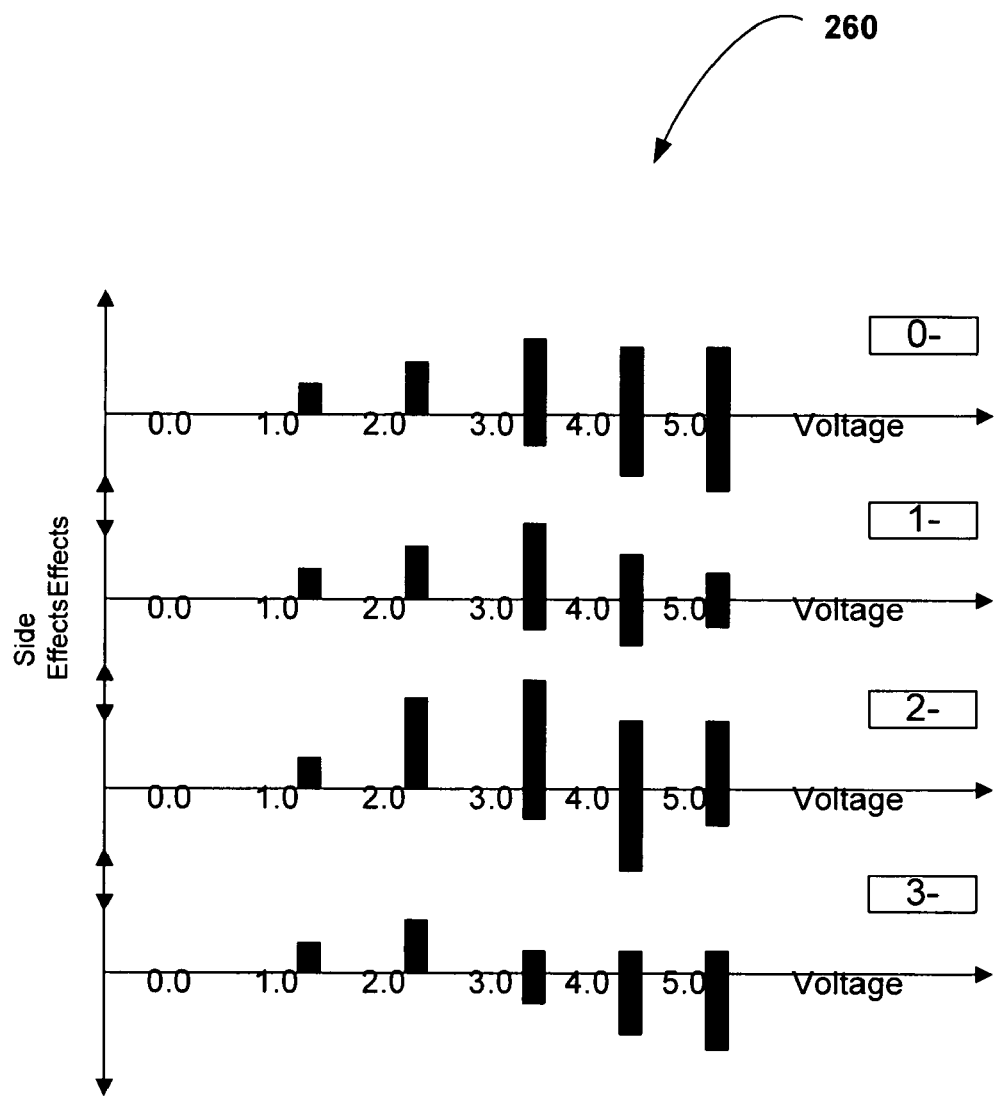

FIGS. 18-20 are conceptual diagrams illustrating examples of graphical guidance information that may be provided to a clinician by a clinician programmer based on a stored programming history. For example, FIG. 18 illustrates a graph 240 that depicts the therapeutic ranges for various programs in a side-by-side manner. The programs are identified in the figure by their electrode configurations on the x-axis. For example, the configuration "0–" indicates that an electrode at a "0" position on a lead is a cathode, while an indifferent electrode, e.g., the housing of IMD 14, is an anode. With the therapeutic ranges illustrated in this manner, a clinician may be able to more readily identify a desirable program to select for long-term programming of INS.

As other examples, FIG. 19 illustrates a graph 250 that places programs in a region on a two-dimensional therapeutic and side effect scale, while FIG. 20 includes bar graphs for each of a plurality of programs illustrating the magnitude of both therapeutic and side effects as a function of stimulation amplitude. In FIG. 19, the size of the region for each program illustrates the size of the therapeutic range for the program.

Various embodiments of the invention have been described. However, one skilled in the art will appreciate that various modifications may be made to these embodiments without departing from the scope of the invention. For example, although described herein in the context of implantable stimulators, the invention may be practiced in relation to programming of medical devices that are not implanted or are not stimulators.

Further, although guidance information has generally been described herein as being provided by a clinician programmer based on information stored in a programming history, the invention is not so limited. In some embodiments, the clinician programmer may additionally display historical session logs, or generate guidance information based on the historical session logs, alone or in combination with the programming history. Such embodiments may allow a clinician to receive guidance based on all or a larger subset of programs tested on a patient when a smaller subset of information is stored in the programming history, e.g., when only information relating to programs sent home with the patient are stored in the programming history.

These and other embodiments are within the scope of the following claims.

The invention claimed is:

1. A method comprising:
controlling an implantable medical device to deliver therapy to a patient according to each of a plurality of programs with a programming device during a programming session;
recording rating information for each of the plurality of programs during the programming session within the programming device;
receiving selection of a subset of the programs during the programming session;
storing the selected subset of the programs within the implantable medical device, wherein each of the programs within the selected subset of the programs is available to be selected by the patient to control delivery of therapy by the implantable medical device outside of the programming session;

for the selected subset of the programs, storing information identifying the programs and rating information associated with the programs in a programming history for the patient within the implantable medical device; and storing within the implantable medical device information identifying the programs and rating information associated with the programs for each of the plurality of programs as a session log separate from the programming history, wherein the session log is associated with the programming session.

2. The method of claim 1, further comprising:

recording rating information during a subsequent programming session with the programming device;

updating the programming history stored in the implantable medical device to include the rating information.

3. The method of claim 1, wherein storing rating information associated with the programs in a programming history comprises storing a subset of the rating information associated with each of the programs in the programming history within the implantable medical device.

4. The method of claim 3, wherein storing a subset of the rating information comprises storing a therapeutic range for each of the programs, wherein the therapeutic range for a program is determined during the programming session, and based on an amplitude of first effect perception and an amplitude at which side effects are not tolerated.

5. The method of claim 3, wherein storing a subset of the rating information comprises storing information identifying amplitudes at which rating information changed for each of the programs.

6. The method of claim 1, further comprising:

recording physiological sensor information during delivery of therapy according to one of the selected subset of programs within the implantable medical device; and storing the physiological sensor information in association with the one of the selected subset of programs in the programming history within the implantable medical device.

7. The method of claim 1, wherein controlling an implantable medical device to deliver therapy comprises controlling the implantable medical device to deliver one of spinal cord stimulation or deep brain stimulation.

8. The method of claim 1, further comprising:

retrieving the programming history from the implantable medical device during a subsequent programming session;

analyzing the retrieved programming history; and providing guidance information to a user based on the analysis to guide the selection of therapy programs during the subsequent programming session.

9. The method of claim 8, wherein each of the programs includes a respective electrode configuration with a plurality of electrodes selected from an electrode set for delivery of stimulation, wherein analyzing the programming history comprises associating information from the programming history with at least one individual electrode from the electrode set, and wherein providing guidance information comprises providing information relating to the individual electrode.

10. The method of claim 8, wherein providing guidance information comprises displaying a graphical representation of the programming history that includes efficacy and side effect information for a plurality of the programs.

11. The method of claim 8, wherein providing guidance information comprises displaying a graphical representation of the programming history that includes a therapeutic range for each of a plurality of the programs.

12. The method of claim 1, wherein the session log includes information identifying the programs and rating information associated with one or more programs tested during the programming session that are not part of the selected subset of the programs.

13. The method of claim 1, further comprising:

retrieving the programming history and the session log from the implantable medical device during a subsequent programming session;

providing guidance information to a user based on the programming history and the session log to guide the selection of therapy programs during the subsequent programming session.

14. The method of claim 1, wherein the programming session is a first programming session, the plurality of programs is a first set of programs, and the session log is a first session log, and wherein the method further comprises storing information identifying a second set of programs and rating information associated with the second set of programs within the implantable medical device as a second session log separate from the programming history, wherein the second session log is associated with the second programming session.

15. The method of claim 1, wherein the selected subset of the programs includes at least two different programs.

16. The method of claim 1, wherein the programming session is a part of a plurality of programming sessions, wherein the session log is part of a plurality of session logs, and wherein each session log is associated with a respective programming session.

17. A system comprising:

an implantable medical device that delivers a therapy to a patient; and a programming device that controls the implantable medical device to deliver the therapy to the patient according to each of a plurality of programs during a programming session, records rating information for each of the plurality of programs during the programming session, receives selection of a subset of the programs, provides the selected subset of the programs to the implantable medical device, and provides information identifying the programs and rating information associated with the programs to the implantable medical device, wherein the implantable medical device stores the selected subset of the programs provided by the programming device, wherein each of the programs within the selected subset of the programs is available to be selected by the patient to control delivery of therapy by the implantable medical device outside of the programming session, wherein, for the selected subset of the programs, the implantable medical device stores the information identifying the programs and rating information associated with the programs received from the programming device as a programming history for the patient, and wherein the implantable medical device stores the information identifying the programs and rating information associated with the programs for each of the plurality of programs as a session log separate from the programming history, wherein the session log is associated with the programming session.

18. The system of claim 17,
wherein the programming device retrieves the programming history from the implantable medical device during a subsequent programming session, records rating information during the subsequent programming session, updates the programming history to include the rating information, and provides the updated programming history to the implantable medical device, and
wherein the implantable medical device stores the updated programming history.

19. The system of claim 17, wherein the programming device provides a subset of the recorded rating information associated with each of the programs to the implantable medical device, and the implantable medical device stores the subset of the rating information in the programming history.

20. The system of claim 19, wherein the subset of the rating information comprises a therapeutic range for each of the programs, wherein the therapeutic range for a program is determined during the programming session, and based on an amplitude of first effect perception and an amplitude at which side effects are not tolerated.

21. The system of claim 19, wherein the subset of the rating information comprises information identifying amplitudes at which rating information changed for each of the programs.

22. The system of claim 17, wherein the implantable medical device records physiological sensor information during delivery of therapy according to one of the selected subset of programs within the implantable medical device, and stores the sensor information in association with the one of the selected subset of programs in the programming history.

23. The system of claim 17, wherein the implantable medical device delivers one of spinal cord stimulation or deep brain stimulation.

24. The system of claim 17, wherein the programming device retrieves the programming history from the implantable medical device during a subsequent programming session, analyzes the retrieved programming history, and provides guidance information to a user based on the analysis to guide the selection of therapy programs during the subsequent programming session.

25. The system of claim 24,
wherein each of the programs includes a respective electrode configuration with a plurality of electrodes selected from an electrode set for delivery of stimulation, and
wherein the programming device associates information from the programming history with at least one individual electrode from the electrode set, and provides information relating to the individual electrode.

26. The system of claim 24, wherein the programming device displays a graphical representation of the programming history that includes efficacy and side effect information for a plurality of the programs.

27. The system of claim 24, wherein the programming device displays a graphical representation of the programming history that includes a therapeutic range for each of a plurality of the programs.

28. A non-transitory computer-readable medium comprising instructions that cause a programmable processor to:
control an implantable medical device to deliver therapy to a patient according to each of a plurality of programs with a programming device during a programming session;
record rating information for each of the plurality of programs during the programming session within the programming device;
receive selection of a subset of the programs during the programming session;
store the selected subset of the programs within the implantable medical device, wherein each of the programs within the selected subset of the programs is available to be selected by the patient to control delivery of therapy by the implantable medical device outside of the programming session;
for the selected subset of the programs, store information identifying the programs and rating information associated with the programs in a programming history for the patient within the implantable medical device; and
store within the implantable medical device information identifying the programs and rating information associated with the programs for each of the plurality of programs as a session log separate from the programming history, wherein the session log is associated with the programming session.

29. The non-transitory computer-readable medium of claim 28, wherein the instructions that cause a programmable processor to store rating information associated with the programs in a programming history comprise instructions that cause a programmable processor to store a subset of the rating information associated with each of the programs in the programming history with the implantable medical device.

30. The non-transitory computer-readable medium of claim 29, wherein the instructions that cause a programmable processor to store a subset of the rating information comprise instructions that cause a programmable processor to store a therapeutic range for each of the programs, wherein the therapeutic range for a program is determined during the programming session, and based on an amplitude of first effect perception and an amplitude at which side effects are not tolerated.

31. The non-transitory computer-readable medium of claim 28, further comprising instructions that cause a programmable processor to:
record physiological sensor information during delivery of therapy according to one of the selected subset of programs within the implantable medical device; and
store the physiological sensor information in association with the one of the selected subset of programs in the programming history within the implantable medical device.

32. The non-transitory computer readable medium of claim 28, further comprising instructions that cause a programmable processor to:
retrieve the programming history from the implantable medical device during a subsequent programming session;
analyze the retrieved programming history; and
provide guidance information to a user based on the analysis to guide the selection of therapy programs during the subsequent programming session.

* * * * *